United States Patent [19]

Kempf et al.

[11] Patent Number: 4,994,477
[45] Date of Patent: Feb. 19, 1991

[54] HETEROCYCLIC RENIN INHIBITORS

[75] Inventors: Dale J. Kempf, Lake Villa; Saul H. Rosenberg; Jacob J. Plattner, both of Libertyville; Hing L. Shan, Gurnee; Biswanath De, Vernon Hills, all of Ill.

[73] Assignee: Abbott Laboratories, Abbott Park, Ill.

[21] Appl. No.: 173,382

[22] Filed: Mar. 24, 1988

[51] Int. Cl.$^5$ .................. A61K 31/42; C07D 413/02; C07D 413/14
[52] U.S. Cl. .................................. 514/359; 548/229; 548/429
[58] Field of Search ................ 514/411, 359; 548/429, 548/229

[56] References Cited

U.S. PATENT DOCUMENTS

| | | | |
|---|---|---|---|
| 4,153,711 | 5/1979 | Zinnes et al. | 548/429 |
| 4,546,107 | 10/1985 | Tahara et al. | 514/411 |
| 4,548,926 | 10/1985 | Matsueda et al. | 514/19 |
| 4,645,759 | 2/1987 | Luly et al. | 514/18 |
| 4,657,931 | 4/1987 | Baran et al. | 514/616 |
| 4,680,284 | 7/1987 | Luly et al. | 514/18 |
| 4,725,584 | 2/1988 | Luly et al. | 514/19 |
| 4,727,060 | 2/1988 | Buhlmayer et al. | 514/18 |
| 4,765,985 | 8/1988 | Leeson | 514/411 |

FOREIGN PATENT DOCUMENTS

| | | |
|---|---|---|
| 0229667 | 7/1987 | European Pat. Off. . |
| 0230266 | 7/1987 | European Pat. Off. . |
| 1049491 | 10/1983 | U.S.S.R. ............ 548/429 |
| 2103231 | 2/1983 | United Kingdom ........ 548/429 |

OTHER PUBLICATIONS

Matsueda et al., Chem. Lett. 1044 (1985).
T. Kokubu et al., Hypertension 8 (6) (Suppl II), II-11 (1986).
Thaisrivongs et al., J. Med. Chem., 28 1555 (1985).
Thaisrivongs et al., J. Med. Chem 30 976 (1987).
T. Kokubu et al., Hypertension 7 (Suppl. I), I-8 (1985).
G. Hanson et al., Biochem. Biophys. Res. Commun., 132, 155 (1985).
D. Kempf et al., J. Med. Chem. 30 1978 (1987).
J. Luly et al., J. Med. Chem. 30 1609 (1987).

*Primary Examiner*—David B. Springer
*Attorney, Agent, or Firm*—Steven R. Crowley

[57] ABSTRACT

A renin inhibiting compound of the formula:

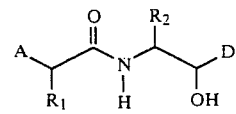

wherein A is a substituent; $R_1$ is loweralkyl, loweralkenyl, alkoxyalkyl, [(alkoxy)alkoxy]alkyl, alkoxycarbonylalkyl, carboxyalkyl, (thioalkoxy)alkyl, benzyl or heterocyclic ring substituted methyl; $R_2$ is hydrogen, loweralkyl, cycloalkylmethyl or benzyl; D is a substituent; or pharmaceutically acceptable salts or esters thereof.

Also disclosed are renin inhibiting compositions, a method of treating hypertension, methods of making the renin inhibiting compounds and intermediates useful in making the renin inhibiting compounds.

7 Claims, No Drawings

HETEROCYCLIC RENIN INHIBITORS

TECHNICAL FIELD

The present invention relates to novel organic compounds and compositions which inhibit renin, processes for making such compounds, synthetic intermediates employed in these processes and a method of treating hypertension with such compounds.

BACKGROUND ART

Renin is a proteolytic enzyme synthesized and stored principally in a specific part of the kidney called the juxtaglomerular apparatus. Any of three different physiologic circumstances may cause the release of renin into the circulation: (a) a decrease in the blood pressure entering or within the kidney itself; (b) a decrease in the blood volume in the body; or (c) a fall in the concentration of sodium in the distal tubules of the kidney.

When renin is released into the blood from the kidney, the renin-angiotensin system is activated, leading to vasoconstriction and conservation of sodium, both of which result in increased blood pressure. The renin acts on a circulating protein, angiotensinogen, to cleave out a fragment called angiotensin I (AI). AI itself has only slight pharamacologic activity but, after additional cleavage by a second enzyme, angiotensin converting enzyme (ACE), forms the potent molecule angiotensin II (AII). The major pharmacological effects of AII are vasoconstriction and stimulation of the adrenal cortex to release aldosterone, a hormone which causes sodium retention. Sodium retention causes blood volume to increase, which leads to hypertension. AII is cleaved by an aminopeptidase to form angiotensin III (AIII), which, compared to AII, is a less potent vasoconstrictor but a more potent inducer of aldosterone release.

Inhibitors of renin have been sought as agents for control of hypertension and as diagnostic agents for identification of cases of hypertension due to renin excess.

With these objectives in mind, the renin-angiotensin system has been modulated or manipulated, in the past, with ACE inhibitors. However, ACE acts on several substrates other than angiotensin I (AI), most notably the kinins which cause such undesirable side effects as pain, "leaky" capillaries, prostaglandin release and a variety of behavorial and neurologic effects. Further, ACE inhibition leads to the accumulation of AI. Although AI has much less vasoconstrictor activity than AII, its presence may negate some of the hypotensive effects of the blockade of AII synthesis.

Inhibition of other targets in the renin-angiotensin system such as AII with compounds such as saralasin can block AII activity, but would leave unimpaired and perhaps enhance the hypertensive effects of AIII.

On the other hand, there are no known side effects which result when renin is inhibited from acting on its substrate. Considerable research efforts have thus been carried out to develop useful inhibitors of renin. Past research efforts have been directed to renin antibodies, pepstatin, phospholipids and substrate analogs such as tetrapeptides and octapeptides to tridecapeptides. These inhibitors either demonstrate poor activity in inhibiting renin production or poor specificity for inhibiting renin only. However, Boger et al. have reported that statine-containing peptides possess potent and specific renin-inhibiting activity (Nature, Vol. 303, p. 81, 1983). In addition, Szelke and co-workers have described polypeptide analogs containing a non-peptide link (Nature, vol. 299, p. 555, 1982) which also cause potent renin inhibition and show a high specificity for this enzyme. Recent patents have disclosed novel small peptide renin inhibitors which contain novel dipeptide isosteres as transition state analogs (Szelke, et al., U.S. Pat. No. 4,609,643; Boger, et al., U.S. Pat. No. 4,668,770; Baran, et al., U.S. Pat. No. 4,657,931; Matsueda, et al., U.S. Pat. No. 4,548,926; Luly, et al., U.S. Pat. No. 4,645,759; and Luly, et al., U.S. Pat. No. 4,680,284).

DISCLOSURE OF THE INVENTION

In accordance with the present invention, there are renin inhibiting compounds of the formula:

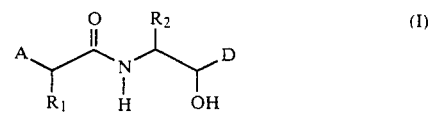

wherein A is

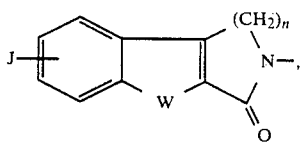

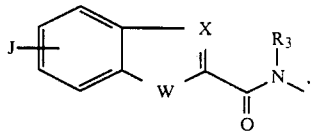

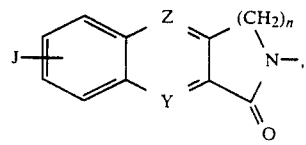

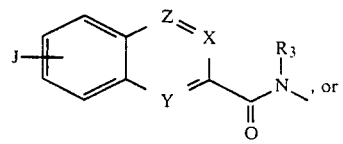

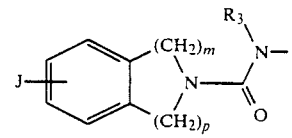

wherein J represents one, two, three or four substituents independently selected from hydrogen, hydroxy, alkoxy, amino, alkylamino, dialkylamino, loweralkyl, thioalkoxy and halo; W is O, S, $CHR_4$ or $NHR_4$ wherein $R_4$ is hydrogen, loweralkyl or arylalkyl; X is N or $CR_5$ wherein $R_5$ is hydrogen, loweralkyl, loweralkenyl, cycloalkylalkyl, cycloalkylalkenyl, arylalkyl, arylalkenyl, aminoalkyl, alkylaminoalkyl or dialkylaminoalkyl; $R_3$ is hydrogen or loweralkyl; n is 1, 2 or 3; Y is $CR_6$ or N wherein $R_6$ is hydrogen, loweralkyl or arylalkyl; Z is $CR_7$ or N wherein $R_7$ is hydrogen, loweralkyl or arylalkyl; m is 0, 1 or 2; p is 1 or 2; $R_1$ is loweralkyl, loweralkenyl, alkoxyalkyl, [(alkoxy)alkoxy]alkyl, alkoxycarbonylalkyl, carboxyalkyl, (thioalkoxy)alkyl, benzyl or heterocyclic substituted methyl; $R_2$ is hydrogen, loweralkyl, cycloalkylmethyl or benzyl; D is $CHR_8R_9$ wherein $R_8$ is hydrogen or hydroxy and $R_9$ is loweralkyl, hydroxyalkyl, alkoxyalkyl, azidoalkyl, aminoalkyl, alkylaminoalkyl, dialkylaminoalkyl, (N-protected)aminoalkyl, (N-protected)(alkyl)aminoalkyl, thioalkoxy, alkylsulfonyl, thioaryloxy, arylsulfonyl, hydrogen, $C(=CH_2)CONHR_{10}$, $C(OH)R_{11}CONHR_{10}$ or $CHR_{11}CONHR_{10}$ wherein $R_{10}$ is loweralkyl, hydroxyalkyl, alkoxyalkyl, aminoalkyl, alkylaminoalkyl or dialkylaminoalkyl and $R_{11}$ is hydrogen, loweralkyl, hydroxyalkyl, haloalkyl or azidoalkyl; or D is

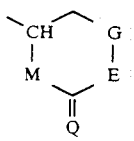

wherein M is O, S or NH; Q is O or S; E is O, S or $NR_{12}$ wherein $R_{12}$ is hydrogen, loweralkyl, hydroxyalkyl, hydroxy, alkoxy, amino or alkylamino; G is absent, $CH_2$, NH or $NR_{13}$ wherein $R_{13}$ is hydrogen or loweralkyl, with the proviso that when G is NH or $NR_{13}$ then $R_{12}$ is loweralkyl or hydroxyalkyl; or pharmaceutically acceptable salts or esters thereof.

The chiral centers of the compounds of the invention may have either the "R" or "S" configuration. The terms "R" and "S" configuration are as defined by IUPAC 1974 Recommendations for Section E, Fundamental Stereochemistry, Pure Appl. Chem. (1976) 45, 13-30.

The term "N-protecting group" or "N-protected" as used herein refers to those groups intended to protect nitrogen atoms against undesirable reactions during synthetic procedures or to prevent the attack of exopeptidases on the final compounds or to increase the solubility of the final compounds and includes but is not limited to acyl, acetyl, pivaloyl, t-butylacetyl, trichloroethoxycarbonyl, t-butyloxycarbonyl(Boc), benzyloxycarbonyl (Cbz) or benzoyl groups or an L- or D-aminoacyl residue, which may itself be N-protected similarly.

The term "loweralkyl" as used herein refers to straight or branched chain alkyl radicals containing from 1 to 6 carbon atoms including but not limited to methyl, ethyl, n-propyl, iso-propyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "loweralkenyl" as used herein refers to a loweralkyl radical which contains at least one carbon-carbon double bond.

The term "arylalkyl" as used herein refers to an aryl group appended to an loweralkyl radical including but not limited to benzyl, 1- and 2-naphthylmethyl, halobenzyl and alkoxybenzyl.

The term "arylalkenyl" as used herein refers to an aryl group appended to a loweralkenyl radical.

The term "aminoalkyl" as used herein refers to $-NH_2$ appended to a loweralkyl radical.

The term "hydroxyalkyl" as used herein refers to $-OH$ appended to a loweralkyl radical.

The term "alkylamino" as used herein refers to a loweralkyl radical appended to an NH radical.

The term "cycloalkyl" as used herein refers to an aliphatic ring having 4 to 7 carbon atoms.

The term "cycloalkylalkyl" as used herein refers to a cycloalkyl group appended to a loweralkyl radical, including but not limited to cyclohexylmethyl.

The term "cycloalkylalkenyl" as used herein refers to a cycloalkyl group appended to a loweralkenyl radical.

The term "aryl" as used herein refers to a substituted or unsubstituted carbocyclic aromatic ring substituted with at least one substituent selected from the group alkoxy, thioalkoxy, loweralkyl, amino, (N-protected)amino, alkylamino, dialkylamino, hydroxy, halo, mercapto, nitro, carboxaldehyde, carboxyl, alkoxycarbonyl and carboxamide, including but not limited to phenyl, naphthyl, halophenyl and alkoxyphenyl.

The term "heterocyclic ring substituted methyl" refers to a heterocyclic group appended to a methylene radical, including but not limited to 4-imidazolylmethyl, 2-thienylmethyl, pyrazolylmethyl and 4-thiazolylmethyl.

The terms "alkoxy" and "thioalkoxy" as used herein refer to $R_{14}O-$ and $R_{14}S-$, respectively, wherein $R_{14}$ is a loweralkyl group.

The term "alkoxyalkyl" as used herein refers to an alkoxy group appended to a loweralkyl radical.

The term "(thioalkoxy)alkyl" as used herein refers to thioalkoxy appended to a loweralkyl radical.

The term "dialkylamino" as used herein refers to $-NR_{16}R_{17}$ wherein $R_{16}$ and $R_{17}$ are independently selected from loweralkyl groups.

The term "[(alkoxy)alkoxy]alkyl" refers to an alkoxy group appended to an alkoxy group which is appended to a loweralkyl radical.

The term "N-protected aminoalkyl" as used herein refers to $NHR_{20}$ appended to a loweralkyl group, wherein $R_{20}$ is an N-protecting group.

The term "alkylaminoalkyl" as used herein refers to $NHR_{21}$ appended to a loweralkyl radical, wherein $R_{21}$ is a loweralkyl group.

The term "(N-protected)(alkyl)aminoalkyl" as used herein refers to $NR_{20}R_{21}$, which is appended to a loweralkyl radical, wherein $R_{20}$ and $R_{21}$ are as defined above.

The term "dialkylaminoalkyl" as used herein refers to $NR_{22}R_{23}$ is appended to a loweralkyl radical wherein $R_{22}$ and $R_{23}$ are independently selected from loweralkyl.

The term "carboxyalkyl" as used herein refers to a carboxylic acid group (—COOH) appended to a loweralkyl radical.

The term "alkoxycarbonylalkyl" as used herein refers to $R_{24}COR_{25}-$ wherein $R_{24}$ is an alkoxy group and $R_{25}$ is a loweralkyl radical.

The term "(heterocyclic)alkyl" as used herein refers to a heterocyclic group appended to a loweralkyl radical, including but not limited to imidazolylalkyl, thienylalkyl, pyrazolylalkyl and thiazolylalkyl.

The term "azidoalkyl" as used herein refers to $-N_3$ appended to a loweralkyl radical.

The term "alkylsulfonyl" as used herein refers to $R_{26}S(O)-$ wherein $R_{26}$ is a loweralkyl residue.

The term "thioaryloxy" as used herein refers to $R_{27}S-$ wherein $R_{27}$ is a substituted or unsubstituted carbocyclic or heterocyclic aromatic ring.

The term "arylsulfonyl" as used herein refers to $R_{28}S(O)-$ wherein $R_{28}$ is a substituted or unsubstituted carbocyclic or heterocyclic aromatic ring.

The term "halo" as used herein refers to Cl, Br, F or I substituents.

The term "haloalkyl" as used herein refers to a halo group appended to a loweralkyl radical.

The term "O-protecting group" as used herein refers to a substituent which protects hydroxyl groups and includes but is not limited to substituted methyl ethers, for example, methoxymethyl, benzyloxymethyl, 2-methoxyethoxymethyl, 2-(trimethylsilyl)ethoxymethyl and tehahydropyranyl; substituted ethyl ethers, for example, 2,2,2-trichloroethyl, t-butyl, benzyl and triphenylmethyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates.

The term "heterocyclic ring" or "heterocyclic" as used herein refers to any 5- or 6-membered ring containing from one to three heteroatoms selected from the group consisting of nitrogen, oxygen, and sulfur; wherein the 5-membered ring has 0-2 double bonds and the 6-membered ring has 0-3 double bonds; wherein the nitrogen and sulfur heteroatoms may optionally be oxidized; wherein the nitrogen heteroatom may optionally be quaternized; and including any bicyclic group in which any of the above heterocyclic rings is fused to a benzene ring. Heterocyclics in which nitrogen is the heteroatom are preferred. Fully saturated heterocyclics are also preferred. Preferred heterocyclics are: pyrryl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl.

Saturated heterocyclics may be unsubstituted, monosubstituted or disubstituted with hydroxy, oxo, amino, alkylamino, dialkylamino, alkoxy, thioalkoxy, polyalkoxy or loweralkyl. Unsaturated heterocyclics may be unsubstituted or monosubstituted with hydroxy, amino, alkylamino, dialkylamino, alkoxy, thioalkoxy, polyalkoxy or loweralkyl.

The most preferred heterocyclics are as follows:

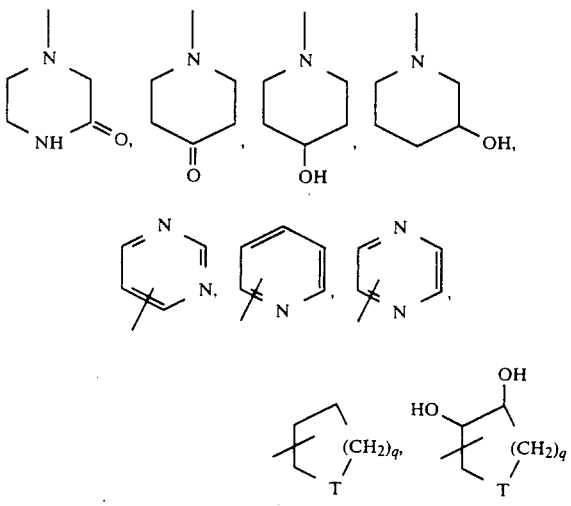

wherein q is 1 or 2 and T is N, NH, O, S, provided that T is the point of connection only when T is N,

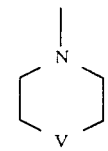

wherein V is NH, N-loweralkyl, O, S, or $SO_2$, or

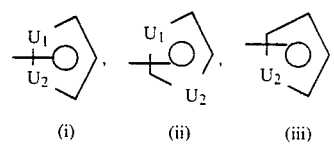

wherein the symbols (i), (ii) and (iii) represent 5-membered heterocycles containing one or more heteroatoms and containing 2 double bonds; wherein $U_1$ is N, O, or S and not the point of connection and $U_2$ is N when it is the point of connection and NH, O or S when it is not the point of connection.

The terms "Glu", "His", "Leu", "Nle", "Ala" and "Gly" as used herein refer to glutamic acid, histidine, leucine, norleucine, alanine and glycine respectively.

The compounds of the invention a my be made as shown in Schemes I-V. The syntheses of segments containing substituents D are described in the Examples or have previously been described (Kempf, et al., J. Med. Chem. 1987, 30, 1978; Luly, et al., J. Med. Chem. 1987, 30, 1609).

In particular, the process shown in Scheme I discloses the esterification of acid[I] to give benzyl ester [II]. Formylation of [II] leads to aldehyde [III] which is condensed with an aminoester under reductive conditions to yield the alkylated amine [IV]. Removal of the benzyl ester by hydrogenolysis, followed by intramolecular acylation using carbodiimide activation leads to the tricyclic structure [V]. Hydrolysis of the methyl ester gives a lithium salt, which is combined with aminoalcohol [VI] using a carbodiimide coupling to yield the renin inhibitor [VII].

The processes shown in Schemes II and III disclose the carbodiimide coupling of aromatic or heteroaromatic acids [VIII] and [XI] to the amine [IX] to give the renin inhibitors [X] and [XII], respectively.

The process shown in Scheme IV discloses the formylation of ethyl ester [XIII] to give aldehyde [XIV]. Homologation of [XIV] leads to the aldehyde [XV]. A second homologation under the same conditions gives the aldehyde [XVI]. Condensation of [XIV], [XV] or [XVI] with an amine under reductive conditions leads to [XVII], which is hydrolyzed and cyclized using carbodiimide activation to give the renin inhibitor [XVIII].

The process shown in Scheme V discloses the reaction of amine [XIX] with phosgene to give carbamoyl chloride [XX]. Treatment of [XX] with aminoester [XXI] in the presence of triethylamine leads to urea [XXII]. Removal of the benzyl ester of [XXII] followed by carbodiimide coupling to aminoalcohol [VI] gives the renin inhibitor [XXIII].

Application of each of these Schemes to materials containing various substituents J is expected to proceed to give substituted renin inhibitors.

Scheme I
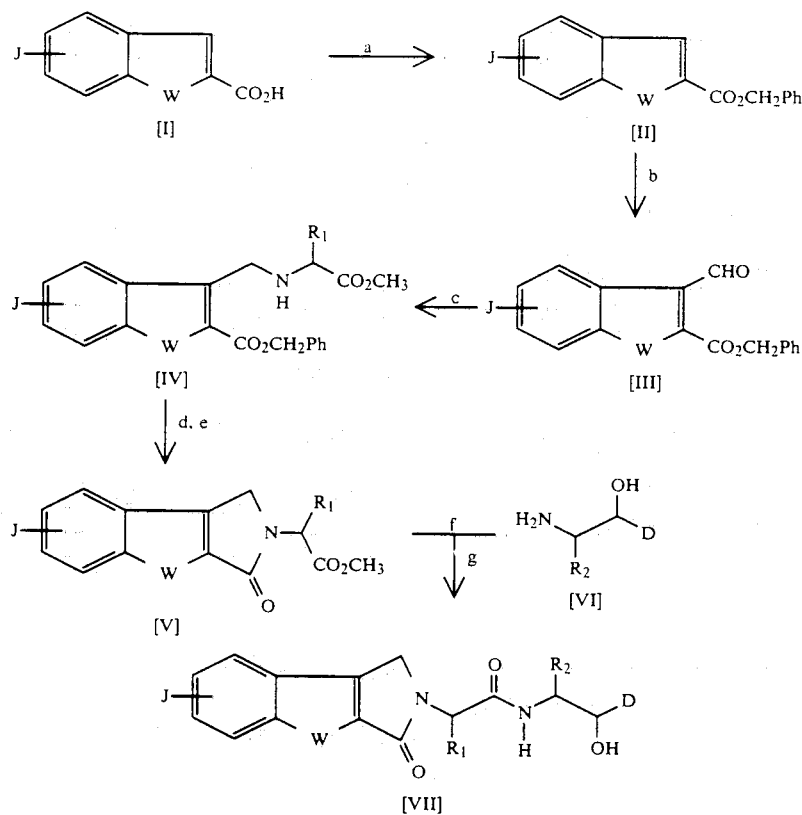
a: PhCH₂OH, DCC, DMAP; b: PhN(CH₃)CHO, POCl₃; c. H₂NCHR₁CO₂CH₃, NaCNBH₃, NaOAc; d: H₂, Pd/C; e: EDAC, DMAP; f: LiOH; g: EDAC, HOBT.
Scheme II
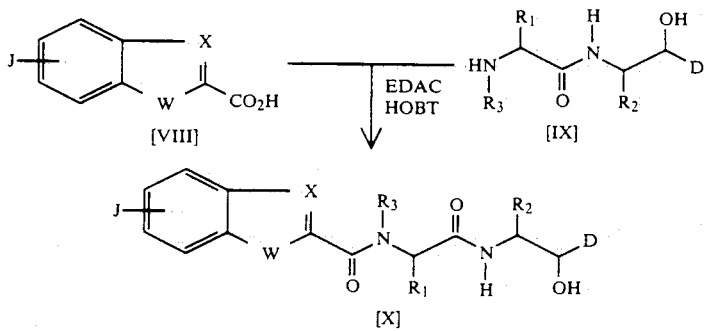
Scheme III
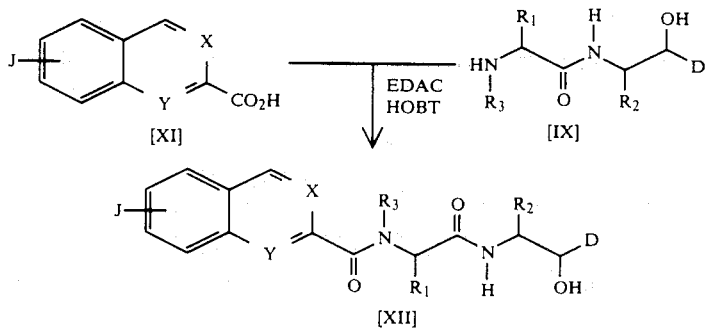

Scheme IV

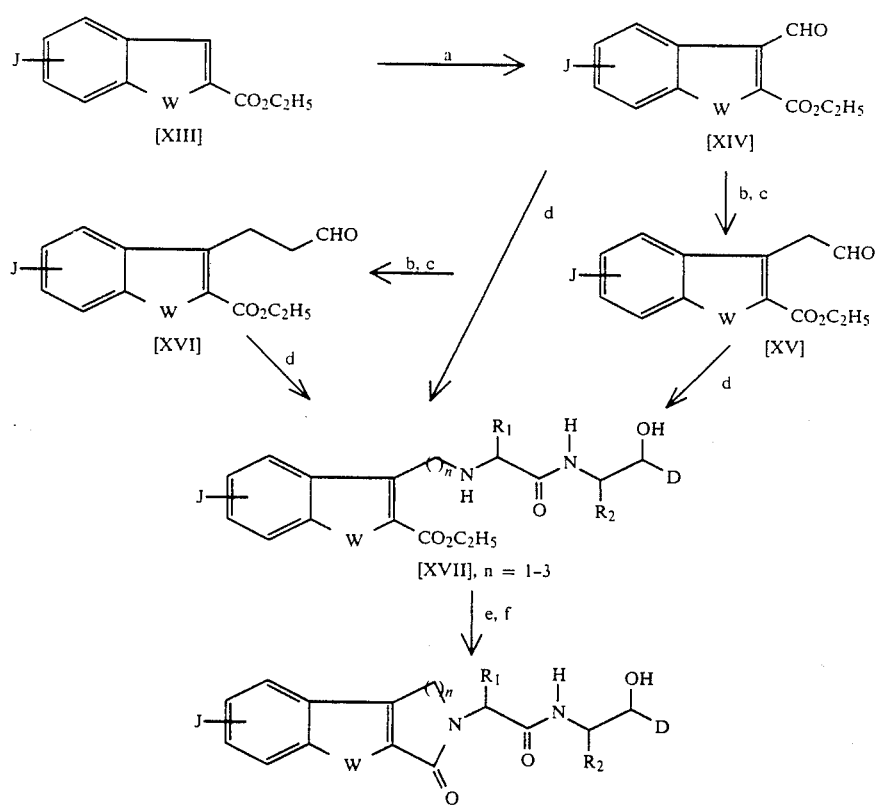

a: PhN(CH₃)CHO, POCl₃; b: CH₃OCH=PPh₃; c: HCl, THF; d: H₂NCHR₁CONHCHR₂CHOHD, NaCNBH₃, NaOAc; e: NaOH; f: EDAC, DMAP.

Scheme V

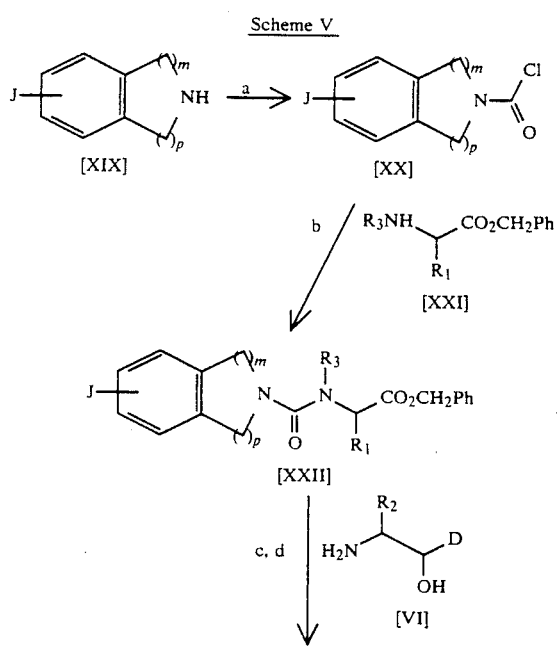

-continued
Scheme V

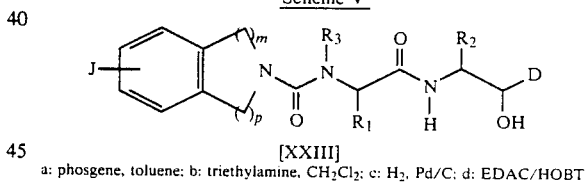

a: phosgene, toluene; b: triethylamine, CH₂Cl₂; c: H₂, Pd/C; d: EDAC/HOBT

EXAMPLE 1

4(S)-t-Butyloxycarbonylamino-5-cyclohexyl-3(R,S)-hydroxy-1-pentene

To a stirred −78° C. solution of Boc-cyclohexylalanine methyl ester (10.2 g, 35.8 mmol) in dry toluene (60 ml) was added diisobutylaluminum hydride (34 ml of a 1.5M solution in toluene). After 30 min, vinyl magnesium bromide (108 ml of 1M solution in tetrahydrofuran (THF)) was added. After stirring for 15 h at 0° C., the mixture was carefully quenched with methanol, treated with Rochelle salts (22 ml of saturated aqueous solution in 140 ml H₂O), and filtered. After extracting the solids 5 times with ethyl acetate, the extracts and filtrate were combined and the organic phase was washed with brine, dried, filtered and evaporated to an oil (10.2 g). Chromatography on silica gel eluting with hexane/ethyl acetate mixtures provided 6.1 g (60%) of the desired product.

Anal Calcd. for C₁₆H₂₉NO₃·¼H₂O: C, 66.8; H 10.3; N 4.9. Found: C, 66.9; H, 10.2; N, 4.7.

EXAMPLE 2

4(S)-Cyclohexylmethyl-5(R,S)-vinyl-2-oxazolidinone

The resultant product of Example 1 (2.80 g, 9.88 mmol) in dry dimethylformamide (DMF) (50 ml) was added to a stirred suspension of NaH (593 mg of a 60% dispersion in oil, 14.8 mmol, hexane washed) in dry DMF (50 ml). After 3 h, the mixture was quenched (750 ml water+100 ml brine) and extracted with ether (5×100 ml). The combined organic phase was washed with brine (3×50 ml), dried (MgSO$_4$), filtered and evaporated to an oil (2.23 g). The NMR spectrum of the crude product revealed an 82:18 mixture of 5S:5R diastereomers. Silica gel chromatography gave 80% recovery of pure diastereomers. 5S:

Anal. Calcd. for $C_{12}H_{19}NO_2$: C, 68.9; H, 9.1; N, 6.7. Found: C, 68.4; H, 9.2; N, 6.5. Mass spectrum: $(M+1)^+ =210$. 5R: Mass spectrum: $(M+1)^+ =210$.

EXAMPLE 3

(3S,4S)-3-Hydroxy-4-amino-5-cyclohexyl-1-pentene

To the resultant 5S-diastereomer from Example 2 (2.06 g, 9.84 mmol) in dioxane (180 ml) and water (120 ml) was added barium hydroxide octahydrate (6.24 g, 19.8 mmol). The mixture was refluxed for 18 h, cooled, filtered, concentrated, taken up in water and extracted with ethyl acetate which was dried over Na$_2$SO$_4$ and evaporated to afford 1.64 g (91%) of the desired product, m.p.: 59°-61° C.

Anal. Calcd. for $C_{11}H_{21}NO$: C, 72.08; H, 11.55; N, 7.64. Found: C, 71.67; H, 11.68; N, 7.36.

EXAMPLE 4

(3S,4S)-3-Hydroxy-4-tert-butyloxycarbonylamino-5-cyclohexyl-1-pentene

To the resultant compound from Example 3 (1.62 g, 8.84 mmol) in methylene chloride (20 ml) was added di-tert-butyldicarbonate (1.93 g, 8.84 mmol). The mixture was stirred for 14 h, diluted with ethyl acetate, washed sequentially with 0.5M H$_3$PO$_4$, saturated NaHCO$_3$ solution and brine, then dried over Na$_2$SO$_4$ and evaporated to afford 2.51 g (100%) of the desired compound.

EXAMPLE 5

(3S,4S)-3-Methoxyethoxymethoxy-4-tert-butyloxycarbonylamino-5-cyclohexyl-1-pentene To the resultant compound from Example 4 (2.51 g, 8.84 mmol) in methylene chloride (20 ml) was added diisopropylethylamine (4.60 ml, 26.4 mmol) and methoxyethoxychloromethane (3.00 ml, 26.3 mmol). After stirring at room temperature for 24 h the mixture was concentrated, diluted with ethyl acetate, washed with 0.5M H$_3$PO$_4$, saturated NaHCO$_3$ solution, then brine, dried over Na$_2$SO$_4$, and evaporated. Chromatography on silica gel with ethyl acetate/hexane mixtures afforded 2.63 g (80%) of the desired product as an oil. EI-MS: $M^+ =371$.

EXAMPLE 6

(2RS,3R,4S)-3-Methoxyethoxymethoxy-4-tert-butyloxycarbonylamino-5-cyclohexyl-1,2-oxopentane To the resultant compound from Example 5 (5.41 g, 14.56 mmol) in methylene chloride (50 ml) was added 3-chloroperbenzoic acid (6.28 g). After stirring at room temperature for 60 h the mixture was concentrated, diluted with ethyl acetate, washed with cold 1:1 15% aqueous Na$_2$SO$_3$ solution/saturated NaHCO$_3$ solution (2×200 ml), saturated NaHCO$_3$ solution (3×100 ml) then brine (1×100 ml), dried over Na$_2$SO$_4$, and evaporated to afford 4.57 g (81%) product as an oil. EI-MS: $M^+ =387$.

EXAMPLE 7

(2'S,1'R,5S)-3-Ethyl-5-(1'-methoxyethoxymethoxy-2'-tert-butyloxycarbonylamino-3'-cyclohexylpropyl)-oxazolidin-2-one To the resultant compound from Example 6 (310 mg, 0.80 mmol) in isopropanol (5 ml) was added ethylamine (200 mg, 4 mmol). The mixture was heated at 70° C. for 48 h, evaporated and dissolved in methylene chloride (5 ml). To this solution was added triethylamine (0.34 ml, 2.4 mmol) and phosgene in toluene (1.0 ml, 1.2 mmol, 12.5% solution). After 2 h the mixture was diluted with ethyl acetate, washed with 0.5M H$_3$PO$_4$, saturated NaHCO$_3$ solution then brine, dried over Na$_2$SO$_4$ and evaporated. Chromatography of the residue on silica gel with 1:1 ethyl acetate/hexane provided 14.3 mg (4%) of the 5R isomer followed by 63.0 mg (17%) of the desired 5S isomer, both as oils.

5S-Isomer: $^1$H-NMR (CDCl$_3$,TMS) δ 4.83 (d,1H), 4.80 (d,1H), 4.58 (m,1H), 3.49 (s,3H), 1.43 (s,9H), 1.15 (t,3H).

5R-Isomer: MS $(M+H)^+ =459$.

EXAMPLE 8

(2'S,1'R,5S)-3-Methoxy-5-(1'-methoxyethoxymethoxy-2'-tert-butyloxycarbonylamino-3'-cyclohexylpropyl)-oxazolidin-2-one Using the procedure of Example 7 but replacing the ethyl amine with equal parts of methoxyamine hydrochloride and sodium bicarbonate gives the desired compound.

EXAMPLE 9

(2RS,3R,4S)-1,2-Dihydroxy-3-methoxyethoxymethoxy-4-tert-butyloxycarbonylamino-5-cyclohexylpentane To the resultant compound from Example 5 (1.00 g, 2.69 mmol) in tetrahydrofuran (20 ml) at 0° C. was added osmium tetroxide (0.75 ml of a 2.5% solution in tert-butanol) and N-methylmorpholine N-oxide (347 mg, 2.95 mmol). The mixture was stirred at room temperature 16 h, diluted with ethyl acetate, washed with NaHSO$_3$ solution, saturated NaHCO$_3$ solution and brine, then dried over Na$_2$SO$_4$ and evaporated. Chromatography of the residue on silica gel with methanol/methylene chloride mixtures provided 887 mg (81%) of the desired product.

Anal. Calcd. for $C_{20}H_{39}NO_7 \cdot 0.3 H_2O$: C, 58.46; H, 9.71; N, 3.41. Found: C, 58.69; H, 9.53; N, 3.41.

EXAMPLE 10

(2'S,1'R,5S)-2-Oxo-4-(1'-methoxyethoxymethoxy-2'-tert-butyloxycarbonylamino-3'-cyclohexylpropyl)-dioxolane The resultant compound of Example 9 in methylene chloride at 0° C. was treated with triethylamine then phosgene in toluene. The mixture was stirred at 0° C. for 1 h, then at room temperature for 3 h, poured into ethyl acetate, washed with 0.5M H$_3$PO$_4$, saturated NaHCO₃ solution and brine, then dried over Na₂SO₄ and evaporated to afford the desired product as an oil.

EXAMPLE 11

2R,3R,4S)-1-Benzyloxycarbonylethylamino-2-hydroxy-3-methoxyethoxymethoxy-4-tert-butyloxycarbonylamino-5-cyclohexylpentane Using the procedure of Example 7 with the resultant compound from Example 6 and replacing the phosgene with benzyl chloroformate provided the desired 2R isomer preceded by the 2S isomer.

2R-Isomer: ¹H-NMR (CDCl₃,TMS) δ 7.34 (m,5H), 5.13 (s,2H), 4.95 (d,1H), 4.79 (m,2H), 3.37 (s,3H), 1.43 (s,9H), 1.14 (m,3H).

2S-Isomer: ¹H-NMR (CDCl₃,TMS) δ 7.35 (m,5H), 5.14 (d,1H), 5.12 (d,1H), 4.93 (d,1H), 4.80 (m,2H), 3.38 (s,3H), 1.43 (s,9H), 1.13 (t,3H).

EXAMPLE 12

(2S,3R,4S)-1-Benzyloxycarbonylethylamino-2-azido-3-methoxyethoxymethoxy-4 tert-butyloxycarbonylamino-5-cyclohexylpentane To triphenylphosphine (100.0 mg, 0.381 mmol) in tetrahydrofuran (THF, 0.6 ml) at −78° C. was added diethyl azodicarboxylate (60 μl, 0.38 mmol) in THF (1 ml). To this mixture was added a solution of hydrazoic acid (0.46 mmol) in benzene (1 ml) then the resultant compound from Example 11 (180.0 mg, 0.318 mmol) in THF (1.4 ml) was added. After one hour the mixture was warmed to room temperature, stirred for 16 h, evaporated and chromatographed on silica gel with 20% ethyl acetate in hexane to afford 103.5 mg (55%) of the desired product as an oil. ¹H-NMR (CDCl₃,TMS) δ 7.35 (m,5H), 5.15 (m,2H), 3.38 (s,3H), 1.45 (s,9H), 1.15 (m,3H).

EXAMPLE 13

(2'S,1'R,5S)-3-Ethyl-5-(1'-methoxyethoxymethoxy-2'-tert-butyloxycarbonylamino-3'-cyclohexylpropyl)-imidazolidin-2-one To the resultant compound from Example 12 (99.0 mg, 0.167 mmol) in methanol (2 ml) was added triethylamine (75 μl, 0.54 mmol) and propane 1,3-dithiol (50 μl, 0.50 mmol). After 72 h the mixture was filtered and evaporated, and the crude amino compound was dissolved in toluene (5 ml) and heated to reflux for 72 h. Evaporation and chromatography on silica gel with ethyl acetate/hexane mixtures provided the desired product as an oil. ¹H NMR (CDCl₃) δ 1.12 (t,3H), 1.43 (s,9H), 3.23 (m,2H), 3.39 (s,3H), 3.64 (m,1H), 3.78 (m,1H), 3.94 (m,1H), 4.58 (d,1H), 4.74 (d,1H), 5.47 (s,1H).

EXAMPLE 14

(3S,4S)-3-tert-Butyldimethylsilyloxy-4-tert-butoxycarbonylamino-5-cyclohexyl 1-pentene To the resultant compound from Example 4 (0.264 g, 0.932 mmol) in DMF (4 ml) was added tert-butyldimethylsilyl chloride (0.300 g, 1.99 mmol) and imidazole (0.269 g, 3.95 mmol). The mixture was stirred at room temperature for 12 hours, poured into ethyl acetate and washed sequentially with 0.5M H₃PO₄, saturated NaHCO₃ solution and brine, then dried over Na₂SO₄ and evaporated to afford 0.355 g (96%) of the desired compound. Mass spectrum: (M+H)⁺=398.

EXAMPLE 15

(2RS,3R,4S)-3-tert-Butyldimethylsilyloxy-4-tert-butoxycarbonylamino-5-cyclohexyl-1,2-oxopentane The resultant compound from Example 14 (0.355 g, 0.893 mmol) in methylene chloride (8 ml) was treated with m-chloroperbenzoic acid (0.758 g, 3.51 mmol) and stirred at ambient temperature for 14 hours. The mixture was concentrated, dissolved in ethyl acetate, washed sequentially with cold 10% aqueous Na₂SO₃ solution, saturated NaHCO₃ solution and brine, and then dried over Na₂SO₄ and evaporated to afford 0.374 g (100%) of the desired compound. Mass spectrum: (M+H)⁺=404.

EXAMPLE 16

(2RS,3R,4S)-3-Hydroxy-4-tert-butoxycarbonylamino-5-cyclohexyl-1,2-oxopentane

The resultant compound from Example 15 (2.10 g, 5.07 mmol) was treated with 1M tetrabutylammonium fluoride in tetrahydrofuran (10 ml). The mixture was stirred at 0° C. for 1 hour, poured into ethyl acetate, washed with water and brine, then dried over Na₂SO₄ and evaporated. Chromatography on silica gel (0.5% methanol in chloroform) afforded 1.3 g (74%) of the desired compound. Mass spectrum: (M+H)⁺=300.

EXAMPLE 17

(2S,3R,4S)-1-Azido-2,3-dihydroxy-4-tert-butoxycarbonylamino-5-cyclohexylpentane

The resultant compound from Example 16 (1.12 g, 3.74 mmol), ammonium chloride (0.374 g, 6.98 mmol) and sodium azide (0.580 g, 8.92 mmol) were refluxed in methanol (25 ml) for 12 hours. The mixture was concentrated, then taken up in ethyl acetate, washed with water and brine, dried over Na₂SO₄ and evaporated. Chromatography on silica gel (20% ether in hexane) afforded 0.461 g (36%) of the desired compound followed by 0.323 g (25%) of the 4-R isomer. 4S-Diasteriomer: m.p. 93°–94° C. 4R-Diasteriomer: mass spectrum: (M+H)⁺=343.

EXAMPLE 18

N-(3-Methylbutyl)-4-hydroxy-5-t-butyloxycarbonylamino-6-cyclohexylhex-1-ene-2-carboxamide A solution of N-(3-methylbutyl)-2-methylpropenamide (643 mg, 4.15 mmol) in 25 ml of dry tetrahydrofuran was cooled under an N₂ atmosphere to −78° C. and treated dropwise with 3.28 ml (8.5 mmol) of n-butyllithium in hexane. The resulting solution was warmed to 0° C. for 20 min, recooled to −78° C. and treated with 6.2 ml (6.2 mmol) of chlorotitanium triisopropoxide in hexane. After again warming to 0° C. for 5 min, the dark solution was recooled to −78° C. treated with a solution of N-t-butyloxycarbonylcyclohexylalininal (670 mg, 2.3 mmol) in 5 ml of tetrahydrofuran, stirred for 5 min at −78° C., warmed to 0° C. for 20 min and quenched with saturated aqueous ammonium chloride. The resulting suspension was treated with ca. 50 ml of ether, stirred until the salts became white, extracted with two 100 ml portions of ether, dried over MgSO₄ and concentrated in vacuo. The crude mixture was separated by flash column chromatography using 4:1 chloroform/ethyl acetate to give 249 mg (26%) of the (4S,5S) product (R$_f$0.44), 292 mg (31%) of the (4R,5S)

product ($R_f$ 0.36, 3:2 chloroform/ethyl acetate) and 184 mg (20%) of a ca. 1:1 mixture of the two products.

(4S,5S)-Isomer: $^1$H NMR (CDCl$_3$) δ 0.8–1.9 (m,16H), 0.94 (d,J=6 Hz,6H), 1.43 (s,9H), 2.42 (m,2H), 3.32 (br q,J=7 Hz,2H), 3.62 (m,1H), 3.68 (m,1H), 4.79 (br d,J=9 Hz,1H), 5.08 (br s,1H), 5.43 (s,1H), 5.56 (s,1H), 6.03 (br t,1H). Mass spectrum: M$^+$=410.

EXAMPLE 19

2(S)-t-Butyloxycarbonylamino-1-cyclohexyl-6-methylhept-3-ene

To a stirred −78° C. solution of Boc-cyclohexylalanine methyl ester (40 g, 140 mmol) in anhydrous toluene (250 ml) was added diisobutylaluminum hydride (130M %, 1.5M solution in toluene, 121.4 ml) at a rate to keep the internal temperature below −60° C. After stirring for an additional 20 minutes at −78° C., the aldehyde solution is used immediately as described below.

To a potassium hydride (35% dispersion in oil, 32.09 g) suspension in a 0° C. mixture of anhydrous THF/DMSO (1000 ml/200 ml) under dry N$_2$ was added 1,1,1,3,3,3-hexamethyldisilazane (209M %, 49.07 g) dropwise. After stirring at 0° C. for 1 hour, the resulting solution was added via cannula to a 0° C. flask containing isopentyltriphenylphosphonium bromide (209M %, 125.66 g). The mixture was stirred vigorously for 1 hour at which time it was cooled to −78° C. The −78° C. aldehyde solution prepared above was then added via cannula. After stirring at −78° C. for 15 minutes, the mixture was allowed to slowly warm to room temperature and then heated to 40° C. for 12 hours. The mixture was then cooled to room temperature and quenched with methanol (7.65 ml) followed by aqueous Rochelle salts (100 ml saturated solution and 500 ml H$_2$O). The mixture was then extracted with ethyl acetate (2x). The combined extracts were washed with water and brine. Drying (MgSO$_4$) and evaporating provided crude alkene which was chromatographed on silica gel (ether/hexane) to give 16.5 g (38%) of the desired compound as an 85:15 mixture of cis:trans isomers. Mp=53°–55° C. Mass spectrum: M$^+$=309.

Anal Calcd. for C$_{19}$H$_{35}$NO$_2$: C, 73.7; H, 11.4; N, 4.5. Found: C, 73.8; H, 11.4; N, 4.5.

EXAMPLE 20

2(S)-t-Butyloxycarbonylamino-1-cyclohexyl-3,4-dihydroxy-6-methylheptane: The 3(R)4(S), 3(S)4(S), 3(R)4(R), and 3(S)4(R) Diastereomers To a solution of the resultant compound of Example 19 (8.50, 27.5 mmol) in dry THF (150 ml) were added OsO$_4$ (2.8 ml of a 2.5% solution in t-butanol and N-methylmorpholine N-oxide (9.28 g, 68.7 mmol). After 4 days the mixture was partitioned between ether (200 ml) and brine (100 ml). The aqueous layer was back-extracted with ether (2×100 ml), and the combined organic phase was washed with 10% Na$_2$SO$_3$, 0.1M H$_3$PO$_4$, and brine. Drying (MgSO$_4$) and evaporating provided a residue (10.81 g) which was chromatographed on silica gel to elute a 60% yield of the 4 diols in the following order.

3(R),4(S) Mass spectrum: (M+H)$^+$=344.
Anal Calcd. for C$_{19}$H$_{37}$NO$_4$: C, 66.4; H, 10.9; N, 4.1. Found: C, 66.4; H, 10.8; N, 3.9.
3(S),4(S) Mass spectrum: (M+H)$^+$=344.
Anal Calcd. for C$_{19}$H$_{37}$NO$_4$: C, 66.4; H, 10.9; N, 5.1. Found: C, 66.4; H, 11.1; N, 4.0.
3(R),4(R) Mass spectrum: (M+H)$^+$=344.
3(S),4(R) Mass spectrum: (M+H)$^+$=344.
Anal Calcd. for C$_{19}$H$_{37}$NO$_4$: C, 66.4; H, 10.9; N, 4.1. Found: C, 66.0; H, 10.7; N, 4.0.

EXAMPLE 21

2-t-Butyloxycarbonylamino-1-cyclohexylbut-3-ene

To a stirred suspension of methyltriphenyl phosphonium bromide (10.97 g, 30.70 mmol) in anhydrous tetrahydrofuran (200 ml) at −78° C. (dry ice/acetone bath) under an argon atmosphere, was added n-butyl lithium (19.8 ml of a 1.55M hexane solution) dropwise over the course of 5 min. After 10 min, the −78° C. bath was replaced with a 0° C. bath for 0.5 h, at which time the resulting orange solution was cooled again to −78° C. The solution was then added dropwise by cannula to a stirred −78° C. solution of Boc-cyclohexylalaninal (27.91 mmol) in anhydrous tetrahydrofuran (30 ml) over the course of 0.5 h. The mixture was then allowed to warm to room temperature during a 3 h period after which water (150 ml) was added. Extraction with hexane (4×100 ml) provided a combined organic phase which was washed with brine (100 ml), dried (Na$_2$SO$_4$), and concentrated. Chromatography with ether/hexane (1/9) provided the desired compound. Mass spectrum: (M+H)$^+$=254.

EXAMPLE 22

3-t-Butyloxycarbonylamino-4-cyclohexyl-1,2-oxobutane

To a stirred solution of the resultant compound of Example 21 (2.0 mmol) in dichloromethane (20 ml) was added m-chloroperbenzoic acid (MCPBA, 1.51 g of 80% MCPBA, 7.0 mmol). After 68 h the reaction mixture was cooled to 0° C., and 0° C. 10% Na$_2$SO$_3$ (5 ml) was added with stirring. After 15 min, the solid was filtered off and extracted with dichloromethane. The combined organic phase was washed sequentially with 0° C. 10% Na$_2$SO$_3$ (6 ml), saturated NaHCO$_3$ (2×6 ml), and water (5 ml). Drying (MgSO$_4$), filtering, concentrating and chromatography on 50 g of SiO$_2$ (hexane/ether, 3/1) gave the desired compound. Mass spectrum: (M+H)$^+$=270.

EXAMPLE 23

3-t-Butyloxycarbonylamino-4-cyclohexyl-2-hydroxy-1-isopropylmercaptobutane

To a stirred solution of the resultant compound of Example 22 (0.87 mmol) in methanol (8.7 ml) was added isopropyl mercaptan (0.87 mmol) and triethylamine (0.87 mmol). The resultant solution was refluxed for 2 h and then evaporated to give a residue which was chromatographed on 15 g of 40μ SiO$_2$ (7/3,hexane/ether) to give the desired compound. Mass spectrum: (M+H)$^+$=346.

EXAMPLE 24

3-t-Butyloxycarbonylamino-4-cyclohexyl-2-hydroxy-1-isopropylsulfonylbutane

Treating the resultant compound of Example 23 with 2.5 equivalents of 3-chloroperoxybenzoic acid in dichloromethane, gave the desired compound after workup as described in Example 22. Mass spectrum: (M+H)$^+$=418.

Anal Calcd. for C$_{21}$H$_{33}$NO$_5$S.0.5 H$_2$O: C, 59.10; H, 9.45; N, 3.28. Found: C, 58.90; H, 9.46; N, 3.03.

EXAMPLE 25

2(S)-Amino-1-cyclohexyl-3(R),4(S)-dihydroxy-6-methylheptane Hydrochloride

To 0.17 g (0.50 mmol) of the resultant compound of Example 20 was added 5 ml of 4M HCl in dioxane. After being allowed to stand for 1 h at ambient temperature, the solution was concentrated with two chloroform chasers to give a white solid which was used without further purification.

EXAMPLE 26

Boc-His Amide of 2(S)-Amino-1-cyclohexyl-3(R),4(S)-dihydroxy-6-methylheptane

To a stirred suspension of Boc-His-OH (72 mg, 0.28 mmol) in dry dimethylformamide (3 ml) at $-23°$ C. was added a solution of the resultant compound of Example 25 (0.28 mmol) in dry dimethylformamide (2 ml) containing N-methylmorpholine (29 mg, 0.28 mmol). Hydroxybenzotriazole (HOBT, 58 mg, 0.43 mmol) and N,N'-dicyclohexylcarbodiimide (DCC, 59 mg, 0.28 mmol) were then added sequentially. After 2 h the mixture was allowed to warm to room temperature. After 22 h the mixture was filtered, evaporated, and partitioned between ethyl acetate (18 ml) and saturated aqueous $NaHCO_3$ (6 ml). The layers were separated, and the organic phase was washed with brine (5 ml), dried ($Na_2SO_4$), filtered, and evaporated to a solid which was chromatographed on $SiO_2$ to give the desired compound. Mass spectrum: $M+ =480$.

Anal Calcd. for $C_{25}H_{44}N_4O_5.\frac{3}{4}H_2O$: C, 60.8; H, 9.1; N, 11.3. Found: C, 60.9; H, 9.2; N, 11.0.

EXAMPLE 27

3-Amino-4-cyclohexyl-2-hydroxy-1-isopropylsulfonylbutane Hydrochloride

Using the procedure of Example 25 with the resultant compound of Example 24 gave the desired compound which was used without further purification.

EXAMPLE 28

His Amide of 2(S)-Amino-1-cyclohexyl-3-(R),4(S)-dihydroxy-6-methylheptane Dihydrochloride Using the procedure of Example 25 with the resultant compound of Example 26 gave the desired compound which was used without further purification.

EXAMPLE 29

(4S,5S)-N-(3-Methylbutyl)-5-amino-4-hydroxy-6-cyclohexylhex-1-ene-2-carboxamide Hydrochloride Using the procedure of Example 25 with the resultant compound of Example 18 gave the desired compound which was used without further purification.

EXAMPLE 30

(2S,3R,4S)-1-Azido-2,3-dihydroxy-4-amino-5-cyclohexylpentane Hydrochloride

Using the procedure of Example 25 with the resultant compound of Example 17 gave the desired compound which was used without further purification.

EXAMPLE 31

(2'S,1'R,5S)-3-Ethyl-5-(2'-amino-3-cyclohexyl-1'-hydroxyproply)imidazolidin-2-one Hydrochloride Using the procedure of Example 25 with the resultant compound of Example 13 gave the desired compound which was used without further purification.

EXAMPLE 32

(2'S,1'R,5S)-2-Oxo-4-(2'-amino-3'-cyclohexyl-1'-hydroxypropyl)dioxolane Hydrochloride Using the procedure of Example 25 with the resultant compound of Example 10 gave the desired compound which was used without further purification.

EXAMPLE 33

(2'S,1'R,5S)-3-Methoxy-5-(1'-hydroxy-2'-amino-3'-cyclohexylpropyl)oxazolidin-2-one Hydrochloride Using the procedure of Example 25 with the resultant compound of Example 8 gave the desired compound which was used without further purification.

EXAMPLE 34

(2'S,1'R,5S)-3-Ethyl-5-(1'-hydroxy-2'-amino-3'-cyclohexylpropyl)oxazolidin-2-one Hydrochloride Using the procedure of Example 25 with the resultant compound of Example 7 gave the desired compound which was used without further purification.

EXAMPLE 35

N-(Indolyl-2-carbonyl)-His Amide of 2(S)-Amino-1-cyclohexyl-3(R),4'(S)-dihydroxy-6-methylheptane A solution of 25 mg (0.15 mmol) of indole-2-carboxylic acid, 0.15 mmol of the resultant compound of Example 28, 21 mg (0.15 mmol) of hydroxybenzotriazole, and 34 μl (0.3 mmol) of 4-methylmorpholine in 2.5 ml of dimethylformamide was treated with 30 mg (0.15 mmol) of N-ethyl-N'-2-(dimethylamino)ethylcarbodiimide and stirred at ambient temperature for 16 h. After removal of the solvent in vacuo, the residue was taken up in ethyl acetate, washed sequentially with aqueous $NaHCO_3$, $H_2O$, and concentrated. Purification by silica gel chromatography using 9:1 chloroform:methanol gave 49 mg (61%) of the desired compound (mp 135°–138° C.). $^1H$ NMR ($CDCl_3$) 0.7–1.7 (br envelope), 0.84 (d,J=7 Hz,3H), 0.92 (d,J=7 Hz,3H), 1.88 (m,1H), 3.19 (m,1H), 3.33 (m,1H), 3.45 (m,1H), 4.38 (m,1H), 5.03 (m,1H), 6.82 (s,1H), 7.03 (s,1H), 7.13 (t,J=8 Hz,1H), 7.28 (t,J=8 Hz,1H), 7.42 (d,J=8 Hz,1H), 7.49 (s,1H), 7.64 (d,J=8 Hz,1H), 8.00 (br,1H), 9.95 (br,1H). Mass spectrum: $(M+H)^+=524$.

Anal. Calcd for $C_{29}H_{41}N_5O_4.H_2O$: C, 64.30; H, 8.00; N, 12.93. Found: C, 64.66; H, 7.84; N, 13.00.

EXAMPLE 36

Boc-γ-benzyl-Glu Amide of 2(S)-Amino-1-cyclohexyl-3(R),4(S)-dihydroxy-6-methylheptane Using the procedure of Example 26 but replacing Boc-His-OH with Boc-γ-benzyl-Glu-OH gave the desired compound.

EXAMPLE 37

N-(Indolyl-2-carbonyl)-γ-benzyl-Glu Amide of 2(S)-Amino-1-cyclohexyl-3(R),4(S)-dihydroxy-6-methylheptane Using the procedure of Examples 28 and 35 but replacing the resultant compound of Example 26 with the resultant compound of Example 36 gave the desired compound (mp 166°–169° C.). $^1$H NMR (CDCl$_3$) δ 0.7–2.0 (br envelope), 0.89 (d,J=7 Hz,1H), 0.95 (d,J=7 Hz,1H), 2.28 (m,2H), 2.5–2.7 (m,2H), 3.25 (m,1H), 3.36 (m,1H), 4.15 (br,1H), 4.35 (m,1H), 4.77 (q,J=7 Hz,1H), 5.11 (m,2H), 6.90 (d,J=9 Hz,1H), 7.02 (br s,1H), 7.16 (br t,J=8 Hz,1H), 7.30 (m,6H), 7.43 (d,J=8 Hz,1H), 7.63 (d,J=7 Hz,1H), 7.68 (d,J=8 Hz,1H), 9.46 (br s,1H). Mass spectrum (M+H)$^+$=606.

Anal. Calcd. for C$_{35}$H$_{47}$N$_3$O$_6$·0.25 H$_2$O: C, 68.88; H, 7.84; N, 6.89. Found: C, 68.93; H, 8.01; N, 6.87.

EXAMPLE 38

N-(Indolyl-2-carbonyl)-Glu Amide of 2(S)-Amino-1-cyclohexyl-3(R),4(S)-dihydroxy-6-methylheptane A solution of 30.6 mg (0.051 mmol) of the resultant compound of Example 37 in 1 ml of methanol was treated with 20 mg of 10% palladium on carbon and stirred under a H$_2$ atmosphere for 2 h. After filtration through Celite, the solution was concentrated and the residue was purified by silica gel chromatography using 4:1 chloroform:methanol to give the desired compound (mp 189°–192° C. (dec)). $^1$H NMR (CDCl$_3$/CD$_3$OD) δ 0.7–1.7 (br envelope), 0.85 (J=7 Hz,3H), 0.92 (d,J=7 Hz,3H), 1.85 (m,1H), 2.02 (m,1H), 2.20 (m,1H), 2.42 (m,2H), 3.29 (m,1H), 4.30 (m,1H), 4.38 (m,1H), 7.10 (m,2H), 7.22 (br t,J=8 Hz,1H), 7.33 (m,1H), 7.58 (br d,J=8 Hz,1H). Mass spectrum: (M+H)$^+$=516.

HRMS: Calcd. for C$_{28}$H$_{42}$N$_3$O$_6$: 516.3074. Found: 516.3092.

EXAMPLE 39

Boc-Nle Amide of 2(S)-Amino-1-cyclohexyl-3(R),4(S)-dihydroxy-6-methylheptane

Using the procedure of Example 26 but replacing Boc-His-OH with Boc-Nle-OH gave the desired compound. Mass spectrum: (M+H)$^+$=457.

EXAMPLE 40

N-(Indolyl-2-carbonyl)-Nle Amide of 2(S)-Amino-1-cyclohexyl-3(R),4(S)-dihydroxy-6-methylheptane Using the procedure of Examples 28 and 35 but replacing the resultant compound of Example 26 with the resultant compound of Example 39 gave the desired compound (mp 231°–234° C.). $^1$H NMR (CD$_3$OD) δ 0.7–2.0 (br envelope), 3.10 (m,2H), 3.83 (m,2H), 4.07 (m,1H), 4.28 (m,2H), 4.57 (m,1H), 4.95 (m,1H), 7.07 (br t,J=8 Hz,1H), 7.20 (br s,1H), 7.23 (br t,J=8 Hz,1H), 7.44 (br d,J=8 Hz,1H), 7.62 (br d,J=8 Hz,1H). Mass spectrum: (M+H)$^+$=500.

EXAMPLE 41

N-(1-Methylindolyl-2-carbonyl)-His Amide of 2(S)-Amino-1-cyclohexyl-3(R),4(S)-dihydroxy6-methylheptane Using the procedure of Example 35 but replacing indole-2-carboxylic acid with 1-methylindole-2-carboxylic acid gave the desired compound (mp 121°–126° C. (dec)). $^1$H NMR (CDCl$_3$) δ 0.7–2.0 (br envelope), 0.90 (d,J=7 Hz,3H), 0.97 (d,J=7 Hz,3H), 3.16 (dd,J=15,7 Hz,1H), 3.22 (d,J=8 Hz,1H), 3.28 (dd,J=15,4 Hz,1H), 3.41 (br t,J=9 Hz,1H), 4.08 (s,3H), 4.39 (m,1H), 4.73 (m,1H), 6.47 (br d,J=9 Hz,1H), 6.99 (s,1H), 7.09 (s,1H), 7.18 (ddd,J=8,7,1 Hz,1H), 7.35 (ddd,J=8,7,1 Hz,1H), 7.40 (d,J=8 Hz,1H), 7.65 (d,J=1 Hz,1H), 7.68 (d,J=8 Hz,1H), 8.06 (br,1H). Mass spectrum: (M+H)$^+$=538.

Anal. Calcd. for C$_{30}$H$_{43}$N$_5$O$_4$·0.5 H$_2$O: C, 65.91; H, 8.11; N, 12.81. Found: C, 65.85; H, 8.00; N, 12.71.

EXAMPLE 42

N-(3-Methylindenyl-2-carbonyl)-His Amide of 2(S)-Amino-1-cyclohexyl-3(R),4(S)-dihydroxy-6-methylheptane Using the procedure of Example 35 but replacing indole-2-carboxylic acid with 3-methylindene-2-carboxylic acid gave the desired compound (mp 165°–173° C. (dec)). $^1$H NMR (CDCl$_3$) δ 0.7–2.0 (br envelope), 0.89 (d,J=7 Hz,3H), 0.96 (d,J=7 Hz,3H), 2.57 (br s,3H), 3.11 (dd,J=15,8 Hz,1H), 3.25 (m,2H), 3.41 (m,1H), 3.68 (m,2H), 4.39 (m,1H), 4.73 (m,1H), 6.71 (br d,J=9 Hz,1H), 6.95 (s,1H), 7.37 (m,2H), 7.50 (m,2H), 7.61 (s,1H). Mass spectrum: (M+H)$^+$=537.

HRMS: Calcd. for C$_{31}$H$_{45}$N$_4$O$_4$: 537.3441. Found: 537.3441.

EXAMPLE 43

N-(Benzofuranyl-2-carbonyl)-His Amide of 2(S)-Amino-1-cyclohexyl-3(R),4(S)-dihydroxy-6-methylheptane Using the procedure of Example 35 but replacing indole-2-carboxylic acid with benzofuran-2-carboxylic acid gave the desired compound (mp 134°–137° C.). $^1$H NMR (CDCl$_3$) δ 0.7–2.0 (br envelope), 0.88 (d,J=7 Hz,3H), 0.96 (d,J=7 Hz,3H), 3.16 (dd,J=15,8 Hz,1H), 3.2–3.3 (m,2H), 3.42 (m,1H), 4.45 (m,1H), 4.81 (m,1H), 6.71 (br d,J=9 Hz,1H), 6.94 (s,1H), 7.31 (br t,J=8 Hz,1H), 7.44 (br t,J=8 Hz,1H), 7.51 (d,J=1 Hz,1H), 7.55 (d,J=8 Hz,1H), 7.60 (d,J=1 Hz,1H), 7.69 (d,J=8 Hz,1H), 8.03 (br,1H). Mass spectrum: (M+H)$^+$=525.

Anal Calcd. for C$_{29}$H$_{40}$N$_4$O$_5$·0.75 H$_2$O: C, 64.72; H, 7.77; N, 10.41. Found: C, 64.99; H, 7.62; N, 10.09.

EXAMPLE 44

Benzothiazole-2-carboxylic Acid

A precooled (−78° C.) solution of 7.7 ml (19.2 mmol) of n-butyllithium in 50 ml of dry tetrahydrofuran was treated dropwise with 2.0 ml (18.3 mmol) of benzothiazole. After the addition was complete, the solution was poured into a mixture of excess dry ice in 100 ml of tetrahydrofuran. After being allowed to warm, the resulting solution was treated with water, washed with ether, acidified with HCl, and filtered to give a yellow solid. Digestion with boiling ether followed by filtration gave 1.55 g (47%) of the desired compound as a nearly white solid.

EXAMPLE 45

N-(Benzothiazolyl-2-carbonyl)-His Amide of 2(S)-Amino-1-cyclohexyl-3(R),4(S)-dihydroxy-6-methylheptane Using the procedure of Example 35 but replacing indole-2-carboxylic acid with benzothiazole-2-carboxylic acid gave the desired compound (mp 192°–195° C.). $^1$H NMR (CDCl$_3$/CD$_3$OD) δ 0.7–1.9 (br envelope), 0.86 (d,J=7 Hz,3H), 0.95 (d,J=7 Hz,3H), 3.1–3.3 (m,4H), 4.32 (dd,J=9,4 Hz,1H), 4.86 (t,J=6 Hz,1H), 6.81 (d,J=1 Hz,1H), 7.55 (m,3H), 7.99 (d,J=8 Hz,1H), 8.12 (d,J=8 Hz,1H). Mass spectrum: (M+H)$^+$=542.

Anal Calcd for C$_{28}$H$_{39}$N$_5$O$_4$S: C, 62.08; H, 7.26; N, 12.93; S, 5.92. Found: C, 62.14; H, 7.39; N, 12.48; S, 5.09.

EXAMPLE 46

1-Benzylbenzimidazole

A solution of 4.96 g (42 mmol) of benzimidazole in 250 ml of tetrahydrofuran was cooled under N$_2$ atmosphere to 0° C. and treated sequentially with 2.12 g (44 mmol) of sodium hydride (50% dispersion in oil) and 5.0 ml (42 mmol) of benzyl bromide. The resulting suspension was stirred at ambient temperature for 16 h, washed sequentially with water and saturated brine, dried over MgSO$_4$, and concentrated. The resulting oil was taken up in 75 ml of ethyl acetate, triturated with 300 ml of hexane, and filtered. The mother liquor was concentrated and filtered, and the combined solids were dried in vacuo at 50° C. to give 7.00 g (80%) of the desired compound. $^1$H NMR (CDCl$_3$) δ 5.38 (s,2H), 7.2 (m,2H), 7.3–7.4 (m,6H), 7.83 (br d,1H), 7.96 (br s,1H).

EXAMPLE 47

1-Benzylbenzimidazole-2-carboxylic Acid.

A solution of 2.08 g (10 mmol) of 1-benzylbenzimidazole in 200 ml of dry tetrahydrofuran was cooled under N$_2$ atmosphere to −78° C. and treated with 8.0 ml (20 mmol) of n-butyllithium. The resulting solution was warmed to 0° C. for 0.5 h, recooled to −78° C., and poured into a mixture of excess dry ice in 200 ml of tetrahydrofuran. After being allowed to warm, the solution was treated with 200 ml of water, washed with ether, neutralized, and washed with ether. The aqueous layer was concentrated in vacuo, after which the residue was triturated with 2% methanol in chloroform and filtered. The filtrate was dried over MgSO$_4$ and concentrated to give 2.01 g (80%) of the desired compound as a white powder. Mass spectrum: (M-OH)$^+$=235.

EXAMPLE 48

1-Benzylbenzimidazolyl-2-carbonyl)-His Amide of 2(S)-Amino-1-cyclohexyl-3(R),4(S)-dihydroxy-6-methylheptane Using the procedure of Example 35 but replacing indole-2-carboxylic acid with 1-benzylbenzimidazole-2-carboxylic acid gave the desired compound. $^1$H NMR (CDCl$_3$/CD$_3$OD) δ 0.7–1.9 (br envelope), 0.82 (d,J=7 Hz,3H), 0.86 (d,J=7 Hz,3H), 2.9–3.3 (m), 4.22 (m,1H), 4.59 (m,1H), 6.21 (m,1H), 7.25–7.45 (m), 7.73 (m,1H). Mass spectrum: (M+H)$^+$=615.

EXAMPLE 49

N-(Benzimidazolyl-2-carbonyl)-His Amide of 2(S)-Amino-1-cyclohexyl-3(R),4(S)-dihydroxy-6-methylheptane Using the procedure of Example 38 with the resultant compound of Example 48 gives the desired compound.

EXAMPLE 50

His Amide of (2′S,1′R,5S)-3-Ethyl-5-(1′-hydroxy-2′-amino-3′-cyclohexylpropyl)oxazolidin-2-one Dihydrochloride Using the procedures of Examples 26 and 28 but replacing the resultant compound of Example 25 with the resultant compound of Example 34 gave the desired compound which was used without further purification.

EXAMPLE 51

N-(Indolyl-2-carbonyl)-His-Amide of (2′S,1′R,5S)-3-Ethyl-5-(1′-hydroxy-2′-amino-3′-cyclohexylpropyl)oxazolidin-2one Using the procedure of Example 35 but replacing the resultant compound of Example 28 with the resultant compound of Example 50 gave the desired compound (mp 170°–172° C.) in 58% yield. $^1$H NMR (CD$_3$OD) δ 0.7–1.8 (br envelope) 1.13 (t,J=7 Hz,3H), 3.25 (m,2H), 5.02 (br t,J=8 Hz,1H), 3.57 (dd,J=6,3 Hz,1H), 4.04 (m,1H), 4.22 (m,1H), 4.81 (t,J=7 Hz,1H), 6.88 (d,J=2 Hz,1H), 7.13 (ddd,J=8,7,1 Hz,1H), 7.16 (d,J=1 Hz,1H), 7.29 (ddd,J=8,7,1 Hz,1H), 7.44 (dd,J=8,1 Hz), 7.55 (d,J=1 Hz,1H), 7.68 (br d,J=BHz,1H). Mass spectrum: (M+H)$^+$=551.

Anal. Calcd. for C$_{29}$H$_{38}$N$_6$O$_5$.1.75 H$_2$O: C, 59.83; H,.7 18; N, 14.44. Found: C, 59.69; H, 6.73; N, 14.22.

EXAMPLE 52

Benzyl Indole-2-carboxylate

A solution of 19.9 g (124 mmol) of indole-2-carboxylic acid, 16 ml (155 mmol) of benzyl alcohol, and 3.0 g (25 mmol) of 4-dimethylaminopyridine in 800 ml of dichloromethane was treated with 25.6 g (124 mmol) of N,N′-dicyclohexylcarbodiimide and stirred at ambient temperature for 2.5 h. The resulting mixture was filtered, concentrated in vacuo, taken up in 1 l of ethyl acetate, and filtered. The solution was subsequently washed sequentially with 1N NCl, H$_2$O, saturated NaHCO$_3$, and saturated brine, dried over MgSO$_4$, and concentrated. Recrystallization of the residue from ethyl acetate/hexane gave three crops of crystalline material containing 15.79 g, 11.13 g, and 2.25 g of the desired compound (94%). $^1$H NMR (CDCl$_3$) δ 5.40 (s,2H), 7.26 (br t,1H), 7.3–7.5 (m,8H), 7.69 (br d,1H), 8.9 (br s,1H). Mass spectrum: (M+H)$^+$=252.

Anal. Calcd. for C$_{16}$H$_{13}$NO$_2$: C, 76.48; H, 5.21; N, 5.57. Found: C, 76.13; H, 5.53; N, 5.87.

EXAMPLE 53

Benzyl 3-Formylindole-2-carboxylate

A mixture of 6.5 ml (70 mmol) of phosphorus oxychloride and 9.3 ml (70 mmol) of N-methylformanilide was stirred at ambient temperature. The resulting mixture was diluted with 90 ml of 1,2-dichloroethane, treated with 15.0 g (59.8 mmol) of benzyl indole-2-carboxylate, and heated at reflux for 1 h. After being allowed to cool for 5 min, the warm solution was poured into an ice-cold solution of 60 g of sodium acetate hydrate in 200 ml of water. The resulting mixture was stirred for 1 h, filtered, and the yellow solid was washed twice with water and twice with ether, and air-dried. The filtrate was treated with 400 ml of hexane and filtered. The combined solids were digested with hot ethyl acetate, cooled to 0° C., and filtered to give 13.41 g (80%) of the desired compound as an off-white solid. $^1$H NMR (CDCl$_3$/CD$_3$OD) δ 5.50 (s,2H), 7.3–7.55 (m,8H), 8.38 (d,J=9 Hz,1H). Mass spectrum: (M+H)$^+$ =280.

Anal. Calcd. for C$_{17}$H$_{13}$NO$_3$: C, 73.11; H, 4.69; N, 5.02. Found: C, 72.51; H, 4.74; N, 4.88.

EXAMPLE 54

N-[3-(2-Benzyloxycarbonyl)indolyl]methyl-histidine Methyl Ester

A mixture of 2.00 g (7.17 mmol) of the resultant compound of Example 53, 1.82 g (7.53 mmol) of histidine methyl ester dihydrochloride, 1.42 g (21.5 mmol) of anhydrous sodium acetate, and 0.67 g (10.8 mmol) of sodium cyanoborohydride in 200 ml of isopropyl alcohol was stirred at ambient temperature. After 16 h, an additional 0.22 g portion of sodium cyanoborohydride was added and stirring was continued for 4.5 h. The solvent was removed in vacuo and the residue was taken up in ethyl acetate, washed with saturated aqueous NaHCO$_3$ and with saturated brine, dried over MgSO$_4$, and concentrated. Purification of the residue by silica gel chromatography using 7.5% methanol in chloroform gave 2.83 g (91%) of the desired compound. $^1$H NMR (CDCl$_3$) δ 2.76 (dd,J=15,9 Hz,1H), 3.01 (dd,J=15,4 Hz,1H), 3.55 (dd,J=9,4 Hz,1H), 3.66 (s,3H), 4.78 (s,2H), 5.40 (AA′,2H), 6.74 (br s,1H), 7.19 (m,1H), 7.31 (br s,1H), 7.35–7.5 (m,7H), 7.73 (d,J=9 Hz,1H), 9.05 (br s,1H). Mass spectrum: (M+H)$^+$ =433.

Anal. Calcd. for C$_{24}$H$_{24}$N$_4$O$_4$: C, 66.65; H, 5.59; N, 12.95. Found: C, 66.38; H, 5.84; N, 12.48.

EXAMPLE 55

N-3-(2-Carboxy)indolylmethyl-histidine Methyl Ester

A solution of 12.1 g of the resultant compound of Example 54 and 1.2 g of 10% palladium on carbon in 250 ml of methanol was shaken under 4 atmospheres of H$_2$. After filtration, removal of the solvent in vacuo gave 10.4 g of the desired compound which was used without further purification.

EXAMPLE 56

(1′S)-2-[2-(4-Imidazolyl)-1-(methoxycarbonyl)ethyl]-1,2,3,4-tetrahydropyrrolo[3,4-b]indol-3-one A solution of 5.93 g (17.3 mmol) of the resultant compound of Example 55, 0.42 g (3.5 mmol) of 4-dimethylaminopyridine, and 1.9 ml (17.3 mmol) of 4-methylmorpholine in 40 ml of dimethylformamide was treated with 4.00 g (20.8 mmol) of N-ethyl-N′-(dimethylamino)ethylcarbodiimide and stirred at ambient temperature for 16 h. After removal of the solvent in vacuo, the residue was dissolved in ethyl acetate, washed sequentially with saturated aqueous NaHCO$_3$ and saturated brine, dried over MgSO$_4$, and concentrated. Purification of the residue by silica gel chromatography using 5% methanol in chloroform followed by recrystallization from chloroform/hexane gave 1.76 g (31%) of the desired compound as an off-white solid. $^1$H NMR (CDCl$_3$) δ 3.25 (dd,J=15,11 Hz,1H), 3.42 (dd,J=15,5 Hz,1H), 3.72 (s,3H), 4.48 (AA′,2H), 5.31 (dd,J=11,4 Hz,1H), 6.73 (s,1H), 7.11 (br t,J=7 Hz,1H), 7.25 (br t,J=7 Hz,1H), 7.34 (d,J=1 Hz,1H), 7.47 (d,J=8 Hz,1H), 7.51 (d,J=8 Hz,1H). Mass spectrum: (M+H)$^+$ =325.

EXAMPLE 57

(1′S)-2-[1-Carboxy-2-(4-imidazolyl)ethyl]-1,2,3,4-tetrahydropyrrolo[3,4-b]indol-3-one Lithium Salt A solution of 1.18 g (3.64 mmol) of the resultant compound of Example 56 in 15 ml of 1,4-dioxane was cooled to 0° C. and treated with 8.5 ml (4.25 mmol) of aqueous lithium hydroxide. The resulting solution was stirred at 0° C. for 3.5 h and concentrated in vacuo to give the desired compound as a light yellow solid.

EXAMPLE 58

(1′S,2″S,3″R,4″S)-2-[1-[N-(1-Cyclohexyl-3,4-dihydroxy-6-methyl-2-heptyl)carbamoyl]-2-(4-imidazolyl)ethyl]-1,2,3,4-tetrahydropyrrolo[3,4-b]indol-3-one.

Using the procedure of Example 35 but replacing indole-2-carboxylic acid with the resultant compound of Example 57 and replacing the resultant compound of Example 28 with the resultant compound of Example 25 gave the desired compound (mp 149°–154° C. (dec)) in 24% yield. $^1$H NMR (CDCl$_3$) δ 0.5–1.0 (br envelope), 0.73 (d,J=7 Hz,3H), 0.89 (d,J=7 Hz,3H), 1.2–1.6 (br envelope), 1.84 (m,2H), 3.17 (m,2H), 3.28 (br d,J=8 Hz,1H), 3.47 (dd,J=15,8 Hz,1H), 4.48 (m,1H), 4.57 (br s,1H), 5.56 (br t,J=7 Hz,1H), 6.83 (br s,1H), 7.19 (t,J=7 Hz,1H), 7.33 (m,2H), 7.49 (d,J=7 Hz,1H), 7.51 (br s,1H), 7.61 (d,J=7 Hz,1H), 9.86 (br,1H). Mass spectrum: (M+H)$^+$ =536.

Anal. Calcd. for C$_{30}$H$_{41}$N$_5$O$_4$.0.75 H$_2$O: C, 65.61; H, 7.80; N, 12.75. Found: C, 65.50; H, 7.81; N, 12.69.

EXAMPLE 59

(1′S,2″S,3″R,5′″S)-2-[1-[N-[1-Cyclohexyl-3-hydroxy-3-(3-ethyloxazolidin-2-on-5-yl)-2-propyl]carbamoyl]-2-(4-imidazolyl)ethyl]-1,2,3,4-tetrahydropyrrolo[3,4-b]indol-3-one Using the procedure of Example 35 but replacing indole-2-carboxylic acid with the resultant compound of Example 57 and replacing the resultant compound of Example 28 with the resultant compound of Example 34 gave the desired compound (mp 158°–166° C. (dec)) in 7% yield. $^1$H NMR (CDCl$_3$/CD$_3$OD) δ 0.6–1.0 (br envelope), 1.11 (t,J=7 Hz,3H), 1.35–1.5 (br envelope), 1.66 (m,1H), 3.11 (dd,J=15,7 Hz,1H), 3.24 (qd,J=7,2 Hz,2H), 3.3–3.45 (m,2H), 3.52 (dd,J=9,7 Hz,1H), 3.57 (dd,J=7,3 Hz,1H), 4.06 (m,1H), 4.16 (dt,J=8,6 Hz,1H), 4.61 (AA′,2H), 5.16 (t,J=8 Hz,1H), 6.85 (s,1H), 7.19 (ddd,J=8,7,1 Hz,1H), 7.33 (ddd,J=8,7,1 Hz,1H), 7.51 (d,J=8 Hz,1H), 7.53 (s,1H), 7.62 (d,J=8 Hz,1H). Mass spectrum: (M+H)$^+$ =563.

Anal. Calcd. for C$_{30}$H$_{38}$N$_6$O$_5$.H$_2$O: C, 61.11; H, 7.01; N, 14.25. Found: C, 61.50; H, 6.69; N, 14.08.

EXAMPLE 60

(1′S,2″S,3″R,5′″S)-2-[1-[N-[1-Cyclohexyl-3-hydroxy-3-(3-methoxyoxazolidin-2-on-5-yl)-2-propyl]carbamoyl]-2-(4-imidazolyl)ethyl]-1,2,3,4-tetrahydropyrrolo[3,4-b]indol-3-one Using the procedure of Example 25 but replacing indole-2-carboxylic acid with the resultant compound of Example 57 and replacing the resultant compound of Example 28 with the resultant compound of Example 33 gives the desired

EXAMPLE 61

(1'S,2"S,3"'R,4"'S)-2-[1-[N-[1-Cyclohexyl-3-hydroxy-3-(1-ethylimidizolidin-2-on-4-yl)-2-propyl]carbamoyl]-2-(4-imidazolyl)ethyl]-1,2,3,4-tetrahydropyrrolo[3,4-b]indol-3-one Using the procedure of Example 35 but replacing indole-2-carboxylic acid with the resultant compound of Example 57 and replacing the resultant compound of Example 28 with the resultant compound of Example 31 gives the desired compound.

EXAMPLE 62

(1'S,2"S,3"R,4"'S)-2-[1-[N-[1-Cyclohexyl-3-hydroxy-3-(2-oxodioxolan-4-yl)-2-propyl]carbamoyl]-2-(4-imidazolyl)ethyl]-1,2,3,4-tetrahydropyrrolo[3,4-b]indol-3-one Using the procedure of Example 35 but replacing indole-2-carboxylic acid with the resultant compound of Example 57 and replacing the resultant compound of Example 28 with the resultant compound of Example 32 gives the desired compound.

EXAMPLE 63

(1'S,2"S,3"R,4"S)-2-[1-[N-(5-Azido-1-cyclohexyl-3,4-dihydroxy-2-pentyl)carbamoyl]-2-(4-imidazolyl)ethyl]-1,2,3,4-tetrahydropyrrolo[3,4-b]indol-3-one Using the procedure of Example 35 but replacing indole-2-carboxylic acid with the resultant compound of Example 57 and replacing the resultant compound of Example 28 with the resultant compound of Example 30 gives the desired compound.

EXAMPLE 64

(1'S,2"S,3"'R)-2-[1-[N-[1-Cyclohexyl-3-hydroxy-4-(isopropylsulfonyl)-2-pentyl]carbamoyl]-2-(4-imidazolyl)ethyl]-1,2,3,4-tetrahydropyrrolo[3,4-b]indol-3-one Using the procedure of Example 35 but replacing indole-2-carboxylic acid with the resultant compound of Example 57 and replacing the resultant compound of Example 28 with the resultant compound of Example 27 gives the desired compound.

EXAMPLE 65

(1'S,4"'S,5"S)-2-[1-[N-[6-Cyclohexyl-4-hydroxy-2-[N-(3-methylbutyl)carbamoyl]hex-1-en-5-yl]carbamoyl]-2-(4-imidazolyl)ethyl]1,2,3,4-tetrahydropyrrolo[3,4-b]indol-3-one Using the procedure of Example 35 but replacing indole-2-carboxylic acid with the resultant compound of Example 57 and replacing the resultant compound of Example 28 with the resultant compound of Example 29 gives the desired compound.

EXAMPLE 66

N-[3-(2-Benzyloxycarbonyl)indolyl]methyl-leucine Methyl Ester

Using the procedure of Example 54 but replacing histidine methyl ester dihydrochloride with leucine methyl ester hydrochloride gave the desired compound in 91% yield after silica gel chromatography using 3:1 hexane:ethyl acetate. $^1$H NMR (CDCl$_3$) δ 0.78 (d,J=7 Hz,3H), 0.87 (d,J=7 Hz,3H), 1.43 (m,2H), 1.63 (m,1H), 3.34 (t,J=7 Hz,1H), 3.59 (s,3H), 4.23 (AA',2H), 5.41 (AA',2H), 7.17 (ddd,J=8,6,2 Hz,1H), 7.3–7.5 (m,7H), 7.80 (dd,J=8,0.5 Hz,1H), 8.81 (br s,1H). Mass spectrum: (M+H)$^+$=409.

EXAMPLE 67

N-[3-(2-Carboxy)indolyl]methyl-leucine Methyl Ester

Using the procedure of Example 55 with the resultant compound of Example 66 gave the desired compound in 97% yield.

EXAMPLE 68

(1'S)-2[1-(Methoxycarbonyl)-3-methylbutyl9-1,2,3,4-tetrahydropyrrolo[3,4-b]indol-3-one Using the procedure of Example 56 with the resultant compound of Example 67 gave the desired compound in 76% yield after silica gel chromatography using 2:1 hexane:ethyl acetate. $^1$H NMR (CDCl$_3$) δ 0.99 (d,J=7 Hz,3H), 1.02 (d,J=7 Hz,3H), 1.58 (m,1H), 1.90 (m,2H), 3.72 (s,3H), 4.42 (d,J=17 Hz,1H), 4.67 (d,J=17 Hz,1H), 5.19 (dd,J=10,6 Hz,1H), 7.70 (br t,J=8 Hz,1H), 7.33 (br t,J=8 Hz,1H), 7.55 (br d,J=8 Hz,1H), 7.62 (br d,J=8 Hz,1H), 9.85 (br s,1H). Mass spectrum: (M+H)$^+$=301.

EXAMPLE 69

(1'S)-2-(1-Carboxy-3-methylbutyl)-1,2,3,4-tetrahydropyrrolo[3,4-b]indol-3-one Lithium Salt Using the procedure of Example 57 with the resultant compound of Example 68 gave the desired compound.

EXAMPLE 70

(1'S,2"S,3"R,4"S)-2-[1-[N-(1-cyclohexyl-3,4-dihydroxy-6-methyl-2-heptyl)carbamoyl]-3-methylbutyl]-1,2,3,4-tetrahydropyrrolo[3,4-b]indol-3-one Using the procedure of Example 58 but replacing the resultant compound of Example 57 with the resultant compound of Example 69 gave the desired compound (mp 205°–208° C.) in 83% yield after silica gel chromatography using 3:2 ethyl acetate:chloroform. NMR (CDCl$_3$) δ 0.5–1.7 (br envelope), 0.82 (d,J=7 Hz,3H), 0.94 (d,J=7 Hz,3H), 1.01 (d,J=7 Hz,3H), 1.03 (d,J=7 Hz,3H), 1.94 (m,1H), 2.16 (m,1H), 3.31 (m,2H), 4.14 (m,1H), 4.38 (m,1H), 4.45 (m,1H), 4.53 (br s,2H), 5.23 (dd,J=9,6 Hz,1H), 7.21 (br t,J=7 Hz,1H), 7.28 (br d,1H), 7.35 (ddd,J=8,7,1 Hz,1H), 7.52 (d,J=8 Hz,1H), 7.61 (d,J=8 Hz,1H), 9.64 (s,1H). Mass spectrum: (M+H)$^+$=512.

Anal. Calcd. for C$_{30}$H$_{45}$N$_3$O$_4$·0.25 H$_2$O: C, 69.80; H, 8.88; N, 8.14. Found: C, 69.75; H, 9.10; N, 7.84.

EXAMPLE 71

N-[3-(2-Benzyloxycarbonyl)indolyl]methyl-glycine Methyl Ester

Using the procedure of Example 54 but replacing histidine methyl ester dihydrochloride with glycine methyl ester hydrochloride gave the desired compound (m.p. 74°–75° C.) in 61% yield after silica gel chromatography using 2:1 dichloromethane:ethyl acetate. $^1$H NMR (CDCl$_3$) δ 3.40 (s,2H), 3.67 (s,3H), 4.29 (s,2H), 5.41 (s,2H), 7.18 (ddd,J=8,6,2 Hz,1H), 7.3–7.5 (m,7H), 7.81 (d,J=9 Hz,1H), 8.84 (br s,1H). Mass spectrum: (M+H)$^+$=353.

Anal. Calcd. for C$_{20}$H$_{20}$N$_2$O$_4$: C, 68.17; H, 5.72; N, 7.95. Found: C, 67.98; H, 5.89; N, 7.83.

EXAMPLE 72

N-[3-(2-Carboxy)indolyl]methyl-glycine Methyl Ester

Using the procedure of Example 55 with the resultant compound of Example 71 gave the desired compound in 87% yield, m.p. 202°–204° C. $^1$H NMR (d$_6$-DMSO) 3.72 (s,3H), 3.82 (s,2H), 4.30 (s,2H), 7.04 (t,J=8 Hz,1H), 7.18 (t,J=8 Hz,1H), 7.40 (d,J=8 Hz,1H), 7.59 (d,J=8 Hz,1H), 11.44 (br s,1H).

EXAMPLE 73

2-(Methoxycarbonyl)methyl-1,2,3,4-tetrahydropyrrolo[3,4-b]indol-3-one

Using the procedure of Example 56 with the resultant compound of Example 72 gave the desired compound (m.p. 215°–217° C.) in 31% yield after recrystallization from chloroform. $^1$H NMR (CDCl$_3$) δ 3.79 (s,3H), 4.44 (s,2H), 4.59 (s,2H), 7.20 (t,J=8 Hz,1H), 7.33 (t,J=8 Hz,1H), 7.55 (d,J=8 Hz,1H), 7.62 (d,J=8 Hz,1H), 9.83 (br s,1H). Mass spectrum: (M+H)$^+$ =245.

EXAMPLE 74

2-Carboxymethyl-1,2,3,4-tetrahydropyrrolo[3,4-b]indol-3-one

Lithium Salt

Using the procedure of Example 57 with the resultant compound of Example 73 gave the desired compound.

EXAMPLE 75

(2'S,3'R,4'S)-2-[N-(1-cyclohexyl-3,4-dihydroxy-6-methyl-2-heptyl)carbamoyl]methyl-1,2,3,4-tetrahydropyrrolo[3,4-b]indol-3-one Using the procedure of Example 58 but replacing the resultant compound of Example 57 with the resultant compound of Example 74 gave the desired compound (m.p. 115°–116° C.) in 16% yield after silica gel chromatography using 2% methanol in dichloromethane. NMR (d$_6$-DMSO) δ 0.82 (d,J=7 Hz,3H), 0.89 (d,J=7 Hz,3H), 1.1–1.8 (br envelope), 2.55 (m,1H), 2.99 (m,1H), 3.15 (m,1H), 3.35 (m,2H), 4.20 (m,3H), 4.48 (m,3H), 4.86 (d,J=6 Hz,1H), 7.12 (ddd,J=8,7,1 Hz,1H), 7.26 (ddd,J=8,7,1 Hz,1H), 7.47 (d,J=8 Hz,1H), 7.64 (d,J=8 Hz,1H), 7.83 (d,J=8 Hz,1H), 11.89 (s,1H). Mass spectrum: (M+H)$^+$ =456.

Anal. Calcd. for C$_{26}$H$_{37}$N$_3$O$_4$.H$_2$O: C, 65.94; H, 8.30; N, 8.87. Found: C, 66.21; H, 8.02; N, 8.80.

EXAMPLE 76 dl-β-(4-Thiazolyl)alanine Methyl Ester Dihydrochloride

A solution of 0.50 g (2.04 mmol) of dl-β-(4-Thiazolyl)alanine dihydrochloride (dl connotes a 50/50 mixture of dextrorotatory and levorotatory isomers) in 9 ml of methanol was cooled to 0° C. and treated with 0.21 ml (2.86 mmol) of thionyl chloride. The resulting solution was heated at 55° C. for 16 h. Removal of the solvent in vacuo gave 0.56 g (99%) of the desired compound as a white solid. Mass spectrum: (M+H)$^+$ =187.

Anal. Calcd. for C$_7$H$_{12}$Cl$_2$N$_2$O$_2$.0.5 H$_2$O: C, 31.35; H, 4.89; N, 11.15. Found: C, 31.38; H, 4.62; N, 10.40.

EXAMPLE 77

N-[3-(2-Benzyloxycarbonyl)indolyl]methyl-dl-β-(4-thiazolyl)alanine Methyl Ester

Using the procedure of Example 54 but replacing histidine methyl ester dihydrochloride with β-(4-thiazolyl)alanine methyl ester hydrochloride gave the desired compound in 70% yield. $^1$H NMR (CDCl$_3$) δ 3.11 (dd,J=15,8 Hz,1H), 3.17 (dd,J=15,6 Hz,1H), 3.59 (s,3H), 3.76 (m,1H), 4.28 (AA',2H), 5.36 (s,2H), 6.96 (d,J=2 Hz,1H), 7.13 (ddd,J=8,6,2 Hz,1H), 7.3–7.5 (m,6H), 7.69 (d,J=8 Hz,1H), 8.65 (d,J=2 Hz,1H), 8.81 (br s,1H). Mass spectrum: (M+H)$^+$ =450.

EXAMPLE 78

N-[3-(2-Carboxy)indolyl]methyl-dl-β-(4-thiazolyl)alanine Methyl Ester Dihydrobromide A solution of the resultant compound of Example 77 (7.19 g, 16.0 mmol) in 100 ml of 30% hydrobromic acid in acetic acid was stirred at ambient temperature for 3.25 h, whereupon a light brown precipitate was observed. The solvent was removed in vacuo, and the residue was taken up in water, washed with ether, concentrated in vacuo, diluted with water, and concentrated by lyophilization to give 8.5 g of the desired compound. Mass spectrum: (M+H)$^+$ =360.

EXAMPLE 79

2-[1-(Methoxycarbonyl)-2-(4-thiazolyl)ethyl]-1,2,3,4-tetrahydropyrrolo[3,4-b]indol-3-one Using the procedure of Example 56 with the resultant compound of Example 78 gave the desired compound in 86% yield which was recrystallized from ethyl acetate. $^1$H NMR (CDCl$_3$) δ 3.59 (dd,J=15,11 Hz,1H), 3.70 (dd,J=15,5 Hz,1H), 3.28 (s,3H), 4.52 (s,2H), 5.45 (dd,J=11,5 Hz,1H), 7.12 (m,1H), 7.18 (br t,J=8 Hz,1H), 7.32 (br t,J=8 Hz,1H), 7.53 (br d,J=8 Hz,1H), 7.59 (br d,J=8 Hz,1H), 8.70 (d,J=2 Hz,1H), 9.83 (br s,1H). Mass spectrum: (M+H)$^+$ =342.

EXAMPLE 80

2-[1-Carboxy-2-(4-thiazolyl)ethyl]-1,2,3,4-tetrahydropyrrolo[3,4-b]indol-3-one Lithium Salt Using the procedure of Example 57 with the resultant compound of Example 79 gave the desired compound.

EXAMPLE 81

(1'S,2"S,3"R,4"S)-2-[1-[N-(1-cyclohexyl-3,4-dihydroxy-6-methyl-2-heptyl)carbamoyl]-2-(4-thiazolyl)ethyl]-1,2,3,4-tetrahydropyrrolo[3,4-b]indol-3-one Using the procedure of Example 58 but replacing the resultant compound of Example 57 with the resultant compound of Example 80 gave the desired compound (mp 226°–231° C.) in 11% yield after silica gel chromatography using 3% methanol in dichloromethane. NMR (CDCl$_3$) δ 0.41 (d,J=7 Hz,3H), 0.74 (d,J=7 Hz,3H), 0.8–1.8 (br envelope), 3.05 (m,1H), 3.25 (m,2H), 3.44 (dd,J=14,8 Hz,1H), 3.67 (dd,J=14,8 Hz,1H), 4.3 (m,2H), 4.61 (d,J=17 Hz,1H), 4.76 (d,J=17 Hz,1H), 5.47 (t,J=8 Hz,1H), 7.16 (br t,J=8 Hz,1H), 7.19 (d,J=3 Hz,1H), 7.30 (br t,J=8 Hz,1H), 7.32 (br d,J=9 Hz,1H), 7.41 (d,J=8 Hz,1H), 7.57 (d,J=8 Hz,1H), 8.71 (d,J=3 Hz,1H), 9.41 (s,1H). Mass spectrum: (M+H)$^+$ =553.

HRMS: Calcd. for C$_{30}$H$_{41}$N$_4$O$_4$S: 553.2848. Found: 553.2849.

Anal. Calcd. for C$_{30}$H$_{40}$N$_4$O$_4$S.0.75 H$_2$O: C, 63.64; H, 7.39; N, 9.89. Found: C, 63.53; H, 7.22; N, 9.93.

EXAMPLE 82 dl-β-(3-Pyrazolyl)alanine Methyl Ester Dihydrochloride

Using the procedure of Example 76 but replacing β-(4-thiazolyl)alanine with β-(3-pyrazolyl)alanine gave the desired compound in 96% yield, mp 196°–198° C.

EXAMPLE 83

N-[3-(2-Benzyloxycarbonyl)indolyl]methyl-dl-β-(3-pyrazolyl)alanine Methyl Ester Using the procedure of Example 54 but replacing histidine methyl ester dihydrochloride with β-(3-pyrazolyl)alanine methyl ester hydrochloride gave the desired compound in 76% yield after recrystallization from ethyl acetate/hexane, mp 124°–127° C. $^1$H NMR (d$_6$-DMSO) δ 2.82 (m,2H), 3.45 (s,3H), 4.13 (m,2H), 5.37 (s,2H), 5.91 (m,1H), 7.06 (br t,J=8 Hz,1H), 7.26 (br t,J=8 Hz,1H), 7.35–7.55 (m,6H), 7.73 (br d,J=8 Hz,1H), 11.66 (br s,1H), 12.47 (br s,1H). Mass spectrum: (M+H)$^+$=433.

EXAMPLE 84

N-[3-(2-Carboxy)indolyl]methyl-β-(3-pyrazolyl)alanine Methyl Ester

Using the procedure of Example 55 with the resultant compound of Example 83 gave the desired compound in 96% yield.

EXAMPLE 85

2-[1-(Methoxycarbonyl)-2-(3-pyrazolyl)ethyl]-1,2,3,4-tetrahydropyrrolo[3,4-b]indol-3-one Using the procedure of Example 56 with the resultant compound of Example 84 gave the desired compound in 65% yield after silica gel chromatography using 2% methanol in dichloromethane. $^1$H NMR (CDCl$_3$) δ 3.42 (dd,J=15,10 Hz,1H), 3.57 (dd,J=15,5 Hz,1H), 3.77 (s,3H), 4.49 (AA',2H), 5.41 (dd,J=10,5 Hz,1H), 6.17 (d,J=3 Hz,1H), 7.11 (br t,J=8 Hz,1H), 7.27 (br t,J=8 Hz,1H), 7.39 (br d,J=2 Hz,1H), 7.50 (br t,J=8 Hz,2H). Mass spectrum: (M+H)$^+$=325.

EXAMPLE 86

(1'S)-2-[1-Carboxy-2-(3-pyrazolyl)ethyl]-1,2,3,4-tetrahydropyrrolo[3,4-b]indol-3-one Lithium Salt Using the procedure of Example 57 with the resultant compound of Example 85 gave the desired compound.

EXAMPLE 87

(1'S,2"S,3"R,4"S)-2-[1-[N-(1-Cyclohexyl-3,4-dihydroxy-6-methyl-2-heptyl)carbamoyl]-2-(3-pyrazolyl)ethyl]-1,2,3,4-tetrahydropyrrolo[3,4-b]indol-3-one Using the procedure of Example 58 but replacing the resultant compound of Example 57 with the resultant compound of Example 86 gave the desired compound (mp 152°–161° C.) in 38% yield after silica gel chromatography using 2% methanol in dichloromethane. $^1$H NMR (CDCl$_3$/CD$_3$OD) δ 0.48 (d,J=7 Hz,3H), 0.77 (d,J=7 Hz,3H), 0.8–1.8 (br envelope), 3.06 (m,2H), 3.30 (dd,J=15,9 Hz,1H), 3.43 (dd,J=15,8 Hz,1H), 4.25 (m,2H), 4.60 (d,J=17 Hz,1H), 4.81 (d,J=17 Hz,1H), 5.15 (t,J=8 Hz,1H), 6.18 (d,J=3 Hz,1H), 7.18 (br t,J=8 Hz,1H), 7.32 (br t,J=8 Hz,1H), 7.45 (d,J=3 Hz,1H), 7.49 (d,J=8 Hz,1H), 7.62 (d,J=8 Hz,1H). Mass spectrum (M+H)$^+$=536.

Anal. Calcd. for C$_{30}$H$_{41}$N$_5$O$_4$.H$_2$O: C, 65.08; H, 7.83; N, 12.64. Found: C, 64.97; H, 7.57; N, 12.62.

EXAMPLE 88

(1'RS,2"S,3"R,5'''S)-2-[1-[N-[1-Cyclohexyl-3-hydroxy-3-(3-ethyloxazolidin-2-on-5-yl)-2-propyl]carbamoyl]-2-(4-thiazolyl)ethyl]-1,2,3,4-tetrahydropyrrolo[3,4-b]indol-3-one Using the procedure of Example 35 but replacing indole-2-carboxylic acid with the resultant compound of Example 80 and replacing the resultant compound of Example 28 with the resultant compound of Example 34 gave the desired compound (mp 147°–154° C.) in 30% yield after silica gel chromatography using 3% methanol in dichloromethane. $^1$H NMR (CDCl$_3$) δ 0.65–1.1 (br envelope), 0.81 (t,J=5 Hz,3H), 0.98 (t,J=5 Hz,3H), 0.8–1.7 (br envelope), 2.84 (dq,J=9,5 Hz,1H), 3.02 (m,1H), 3.05 (dq,J=9,5 Hz,1H), 3.13 (dq,J=9,5 Hz,1H), 3.23 (t,J=6 Hz,1H), 3.93 (dd,J=9,5 Hz,1H), 3.50 (m,2H), 3.55 (m,1H), 3.63 (dd,J=9,5 Hz,1H), 3.70 (m,1H), 3.72 (dd,J=9,5 Hz,1H), 3.90 (m,2H), 4.23 (p,J=4 Hz,2H), 4.45 (br d,1H), 4.57 (br d,J=10 Hz,1H), 4.63 (d,J=10 Hz,1H), 4.72 (d,J=10 Hz,1H), 5.37 (d,J=5 Hz,2H), 5.56 (t,J=5 Hz,1H), 7.18 (m,3H), 7.32 (t,J=8 Hz,2H), 7.5–7.6 (m,5H), 8.69 (d,J=2 Hz,1H), 8.76 (d,J=2 Hz,1H). Mass spectrum: (M+H)$^+$=580.

HRMS: Calcd. for C$_{30}$H$_{38}$N$_5$O$_5$S: 580.2593. Found: 580.2595.

EXAMPLE 89

(1'RS,2"S,3"R,5'''S)-2-[1-[N-[1-Cyclohexyl-3-hydroxy-3-(3-ethyloxazolidin-2-on-5-yl)-2-propyl]carbamoyl]-2-(3-pyrazolyl)ethyl]-1,2,3,4-tetrahydropyrrolo[3,4-b]indol-3-one Using the procedure of Example 35 but replacing indole-2-carboxylic acid with the resultant compound of Example 86 and replacing the resultant compound of Example 28 with the resultant compound of Example 34 gave the desired compound (mp 157°–161° C.). $^1$H NMR (CDCl$_3$) δ 0.5–1.3 (br envelope), 3.0–4.4 (br envelope), 4.6–4.9 (m,4H), 5.7–6.1 (m,3H), 6.21 (d,J=3 Hz,1H), 6.30 (d,J=3 Hz,1H), 7.21 (t,J=8 Hz,2H), 7.35 (br t,J=8 Hz,2H), 7.5 (m,2H), 7.60 (d,J=8 Hz,1H), 7.63 (d,J=8 Hz,1H), 7.66 (d,J=8 Hz,2H), 8.33 (br,2H). Mass spectrum: (M+H)$^+$=563.

Anal. Calcd. for C$_{30}$H$_{38}$N$_6$O$_5$.0.5 H$_2$O: C, 63.03; H, 6.88; N, 14.70. Found: C, 62.96; H, 6.89; N, 14.52.

EXAMPLE 90 dl-Nle Amide of 2(S)-Amino-1-cyclohexyl-3(R),4(S)-dihydroxy-6-methylheptane Hydrochloride Using the procedure of Example 25 with the resultant compound of Example 39 gave the desired compound which was used without further purification.

EXAMPLE 91

N-[3-(2-Benzyloxycarbonyl)indolyl]methyl-dl-Nle Amide of 2(S)-Amino-1-cyclohexyl-3(R),4(S)-dihydroxy-6-methylheptane Using the procedure of Example 54 but replacing histidine methyl ester dihydrochloride with the resultant compound of Example 90 gave the desired compound in 62% yield after purification by silica gel chromatography using 1.5:1 hexane:ethyl acetate.

EXAMPLE 92

N-[3-(2-Carboxy)indolyl]methyl-dl-Nle Amide of 2(S)-Amino-1-cyclohexyl-3(R),4(S)-dihydroxy-6-methylheptane Using the procedure of Example 55 with the resultant compound of Example 91 gave the desired compound in 88% yield.

EXAMPLE 93

(1'RS,2"S,3"R,4"S)-2-[1-[N-(1-Cyclohexyl-3,4-dihydroxy-6-methyl-2-heptyl)carbamoyl]pentyl]-1,2,3,4-tetrahydropyrrolo[3,4-b]indol-3-one Using the procedure of Example 56 with the resultant compound of Example 92 gave the desired compound (mp 226°-227° C.) in 51% yield after recrystallization from methanol/chloroform. $^1$H NMR (d$_6$-DMSO) δ 0.50 (d,J=7 Hz,3H), 0.73 (d,J=7 Hz,3H), 0.82 (d,J=7 Hz,3H), 0.88 (t,J=7 Hz,6H), 0.89 (d,J=7 Hz,3H), 0.9-2.0 (br envelope), 2.55 (m,2H), 2.95 (m,2H), 3.1-3.5 (br envelope), 4.12 (m,2H), 4.5 (m,4H), 4.6-5.0 (m,6H), 7.11 (t,J=8 Hz,2H), 7.25 (t,J=8 Hz,2H), 7.44 (d,J=8 Hz,2H), 7.68 (m,3H), 8.12 (br d,J=9 Hz,1H), 11.83 (br s,1H), 11.86 (br s,1H). Mass spectrum: (M+H)$^+$ =512.

Anal. Calcd. for $C_{30}H_{45}N_3O_4 \cdot 0.25 H_2O$: C, 69.80; H, 8.88; N, 8.14. Found: C, 69.75; H, 8.74; N, 8.13.

EXAMPLE 94

2-(1-Ethoxycarbonyl)pentyl-1,2,3,4-tetrahydro-9H-pyrido[3,4-b]indol-1-one

A solution of 0.38 ml (2.8 mmol) of diisopropylamine in 25 ml of dry tetrahydrofuran was cooled under N$_2$ atmosphere to −78° C. and treated with 1.1 ml (2.8 mmol) of n-butyllithium. The resulting solution was warmed to 0° C. for 5 min, recooled to −78° C. and treated with a solution of 250 mg (1.34 mmol) of 1,2,3,4-tetrahydro-9H-pyrido[3,4-b]indol-1-one (J. Chem. Soc. 1960, 4699) in 5 ml of tetrahydrofuran. The solution was allowed to warm to 0° C. followed by treatment with 0.25 ml (1.4 mmol) of ethyl 2-bromohexanoate. The resulting solution was stirred at ambient temperature for 16 h, partitioned between ether and aqueous ammonium chloride, washed with saturated brine, dried over MgSO$_4$, and concentrated. Purification of the residue by silica gel chromatography using 3:1 hexane:ethyl acetate gave 172 mg (39%) of the desired compound as a colorless oil. 1H NMR (CDCl$_3$) δ 0.91 (br t,3H), 1.27 (5,J=7 Hz,3H), 1.4 (m,4H), 1.86 (m,1H), 2.10 (m,1H), 3.10 (m,2H), 3.66 (ddd,J=13,8,6 Hz,1H), 3.81 (ddd,13,8,6 Hz,1H), 4.2 (m,2H), 5.39 (dd,J=10,5 Hz,1H), 7.15 (td,J=7,1 Hz,1H), 7.31 (td,J=7,1 Hz,1H), 7.47 (d,J=7 Hz,1H), 7.60 (d,J=7 Hz,1H), 9.81 (br s,1H).

EXAMPLE 95

2-(1-Carboxy)pentyl-1,2,3,4-tetrahydro-9H-pyrido[3,4-b]indol-1-one Lithium Salt

Using the procedure of Example 57 with the resultant compound of Example 94 gave the desired compound.

EXAMPLE 96

(1'S,2"S,3"R,4"S)-2-[1-[N-(1-Cyclohexyl-3,4-dihydroxy-6-methyl-2-heptyl)carbamoyl]pentyl]-1,2,3,4-tetrahydro-9H-pyrido[3,4,-b indol-1-one Using the procedure of Example 58 but replacing the resultant compound of Example 57 with the resultant compound of Example 95 gave a mixture of two diastereomeric products which were separated by silica gel chromatography using 2:1 hexane:ethyl acetate to give a 30% yield of the desired compound (mp 115°-117° C.). $^1$H NMR (CDCl$_3$/CD$_3$OD) δ 0.7-2.2 (br envelope), 0.85-0.97 (m,18H), 3.06 (m,4H), 3.14 (m,2H), 3.26 (m,2H), 3.70 (m,6H), 4.28 (dd,J=10,4 Hz,2H), 5.15 (t,J=8 Hz,2H), 7.16 (br t,J=8 Hz,2H), 7.33 (br t,J=8 Hz,2H), 7.45 (d,J=8 Hz,2H), 7.61 (d,J=8 Hz,2H), 9.90 (br s,1H). Mass spectrum: (M+H)$^+$ =526.

Anal Calcd. for $C_{31}H_{47}N_3O_4 \cdot 0.25 H_2O$: C, 70.22; H, 9.03; N, 7.92. Found: C, 70.12; H, 9.10; N, 7.65.

EXAMPLE 97

Ethyl 3-Formylindole-2-carboxylate

Using the procedure of Example 53 but replacing benzyl indole-2-carboxylate with ethyl indole-2-carboxylate gave the desired compound in 76% yield as a light pink crystalline solid after recrystallization from ethanol. $^1$H NMR (CDCl$_3$) δ 1.49 (t,J=7 Hz,3H), 4.53 (q,J=7 Hz,2H), 7.3-7.6 (m,4H), 8.49 (d,J=9 Hz,1H), 9.33 (br s,1H). Mass spectrum: (M+H)$^+$ =218.

EXAMPLE 98

[3-(2-Ethoxycarbonyl)indolyl]acetaldehyde

A suspension of 11.95 g (34.9 mmol) of methoxymethyltriphenylphosphonium chloride in 200 ml of anhydrous tetrahydrofuran was cooled to 0° C. under N$_2$ atmosphere and treated dropwise with 14.3 ml (35.8 mmol) of n-butyllithium. The resulting solution was stirred for 15 min, treated with 3.70 g (17 mmol) of the resultant compound of Example 97, and stirred at ambient temperature for 3 h. After concentration of the solvent in vacuo, and the residue was taken up in ethyl acetate, washed sequentially with water and saturated brine, dried over MgSO$_4$, and concentrated. The crude mixture of vinyl ethers was partially purified by silica gel chromatography using 6:1 hexane:ethyl acetate. The mixture (2.98 g, 71%) was subsequently treated with 20 ml of 1M HCl and 40 ml of tetrahydrofuran and heated at reflux for 6 h. After cooling, the solution was partitioned between ether and saturated aqueous NaHCO$_3$, dried over MgSO$_4$, and concentrated. Purification by silica gel chromatography using 4:1 hexane:ethyl acetate gave 1.35 g (48%) of the desired compound which was recrystallized from ethyl acetate/hexane. $^1$H NMR (CDCl$_3$) δ 1.42 (t,J=7 Hz,3H), 4.17 (d,J=2 Hz,2H), 4.42 (q,J=7 Hz,2H), 7.19 (ddd,J=8,7,1 Hz,1H), 7.37 (ddd,J=8,7,1 Hz), 7.43 (br d,J=8 Hz,1H), 7.61 (br d,J=8 Hz,1H), 8.94 (br s,1H), 9.73 (t,J=2 Hz,1H). Mass spectrum: (M+H)$^+$ =232.

EXAMPLE 99

N-[2-[3-(2-Ethoxycarbonyl)indolyl]ethyl]-His Amide of 2(S)-Amino-1-cyclohexyl-3(R),4(S)-dihydroxy-6-methylheptane Using the procedure of Example 54 but replacing the resultant compound of Example 53 with the resultant compound of Example 98 and replacing histidine methyl ester dihydrochloride with the resultant compound of Example 28 gave the desired compound in 89% yield as a 2:1 mixture of diastereomers after silica gel chromatography using 9:1 chloroform:methanol.

EXAMPLE 100

N-[2-[3-(2-Carboxy)indolyl]ethyl]-His Amide of 2(S)-Amino-1-cyclohexyl-3(R),4(S)-dihydroxy-6-methylheptane Sodium Salt A solution of 325 mg (0.546 mmol) of the resultant compound of Example 99 in 8 ml of 1,4-dioxane was treated with 0.45 ml of 0.3M NaOH and stirred at 60° C. for 6 h. The solvent was concentrated in vacuo to give the desired compound which was used without further purification.

EXAMPLE 101

(1'S,2"S,3"R,4"S)-2-[1-[N-(1-Cyclohexyl-3,4-dihydroxy-6-methyl-2-heptyl)carbamoyl]-2-(4-imidazolyl)ethyl]-1,2,3,4-tetrahydro-9H-pyrido[3,4-b]indol-1-one Using the procedure of Example 56 with the resultant compound of Example 100 but replacing 4-dimethylaminopyridine with hydroxybenzotriazole gave the desired compound (mp 153°-159° C.) in 13% yield after purification by silica gel chromatography using 7.5% methanol in chloroform. $^1$H NMR (CDCl$_3$) δ 0.6-1.9 (br envelope), 0.78 (d,J=7 Hz,1H), 0.93 (d,J=7 Hz,3H), 3.0 (m,3H), 3.25 (m,3H), 3.5 (m,1H), 3.83 (m,2H), 4.33 (m,2H), 5.73 (dd,J=10,5 Hz,1H), 6.89 (s,1H), 7.16 (t,J=8 Hz,1H), 7.32 (t,J=8 Hz,1H), 7.43 (m,2H), 7.60 (d,J=8 Hz,1H), 10.05 (br,1H). Mass spectrum: (M+H)+ =550.

Anal Calcd. for C$_{31}$H$_{43}$N$_5$O$_4$.0.5 H$_2$O: C, 66.64: H, 7.94; N, 12.53. Found: C, 66.99; H, 7.94; N, 12.30.

EXAMPLE 102

3-[3-(2-Ethoxycarbonyl)indolyl]propionaldehyde

Using the procedure of Example 98 with the resultant compound of Example 98 gave the desired compound in 40% yield after purification by silica gel chromatography using 4:1 hexane:ethyl acetate. $^1$H NMR (CDCl$_3$) δ 1.42 (t,J=7 Hz,3H), 2.83 (td,J=8,2 Hz,2H), 3.44 (t,J=8 Hz,2H), 4.43 (q,J=7 Hz,2H), 7.18 (ddd,J=8,7,1 Hz,1H), 7.34 (ddd,J=8,7,1 Hz,1H), 7.40 (br d,J=8 Hz,1H), 7.69 (br d,J=8 Hz,1H), 8.76 (br s,1H), 9.86 (t,J=2 Hz,1H). Mass spectrum: (M+H)+ =246.

EXAMPLE 103

N-[3-[3-(2-Ethoxycarbonyl)indolyl]propyl]-His Amide of 2(S)-Amino-1-cyclohexyl-3(R),4(S)-dihydroxy-6-methylheptane Using the procedure of Example 54 but replacing the resultant compound of Example 53 with the resultant compound of Example 102 and replacing histidine methyl ester dihydrochloride with the resultant compound of Example 28 gives the desired compound.

EXAMPLE 104

N-[3-[3-(2-Carboxy)indolyl]propyl]-His Amide of 2(S)-Amino-1-cyclohexyl-3(R),4(S)-dihydroxy-6-methylheptane Sodium Salt Using the procedure of Example 100 with the resultant compound of Example 103 gives the desired compound.

EXAMPLE 105

(1'S,2"S,3"R,4"S)-2-[1-[N-(1-Cyclohexyl-3,4-dihydroxy-6-methyl-2-heptyl)carbamoyl]-2-(4-imidazolyl)ethyl]-1,2,3,4,5,10-hexahydroazepino[3,4-b]indol-1-one Using the procedure of Example 56 with the resultant compound of Example 104 gives the desired compound.

EXAMPLE 106

Boc-(Me)His Amide of (2'S,1'R,5S)-3-Ethyl-5-(1-hydroxy-2-amino-3-cyclohexylpropyl)oxazolidin-2-one To a stirred solution of N$^\alpha$-(t-butyloxycarbonyl)-N$^\alpha$-methyl-N$^{im}$-tosyl-L-histidine [J. Med. Chem. 29, 2088 (1986), 9.15 mmol] and the product from Example 34 (6.1 mmol) in dichloromethane (75 ml) was added 1.28 ml (9.18 mmol) of triethylamine, followed by the slow addition of diethoxyphosphoryl cyanide (1.36 ml, 8.87 mmol). After being stirred at room temperature for 16 h, the reaction mixture was diluted with dichloromethane, and then washed with saturated aqueous NaHCO$_3$. The organic phase was dried (MgSO$_4$) and then concentrated. The residue was chromatographed on silica gel eluting with ethyl acetate/hexane mixtures to give a 75% yield of the coupled product.

The above product was stirred in CH$_3$OH with 5 equivalents of HOBT for 16 h. The reaction mixture was filtered. The filtrate was evaporated to a solid which was taken up in CHCl$_3$, washed with dil NaHCO$_3$, brine, dried, and filtered. The resultant residue after evaporation was chromatographed eluting with 5% CH$_3$OH/CHCl$_3$. The desired product was obtained in 60% yield.

EXAMPLE 107

(N-Methyl)-His Amide of (2'S,1'R,5S)-3-Ethyl-5-(1-hydroxy-2-amino-3-cyclohexylpropyl)oxazolidin-2-one Dihydrochloride Using the procedure of Example 25 with the resultant compound of Example 106 gives the desired compound.

EXAMPLE 108

N-(Indolyl-2-carbonyl)-(N-methyl)-His Amide of (2'S,1'R,5S)-3-Ethyl-5-(1-hydroxy-2-amino-3-cyclohexylpropyl)oxazolidin 2-one Dihydrochloride Using the procedure of Example 35 but replacing the resultant compound of Example 28 with the resultant compound of Example 107 gives the desired compound.

EXAMPLE 109

N-(Quinolinyl-2-carbonyl)-His Amide of (2'S,1'R,5S)-3-Ethyl-5-(1-hydroxy-2-amino-3-cyclohexylpropyl)oxazolidin-2-one Using the procedure of Example 35 but replacing indole-2-carboxylic acid with quinoline-2-carboxylic acid and replacing the resultant compound of Example 28 with the resultant compound of Example 50 gave the desired compound (mp 133°-136° C.) in 50% yield. $^1$H NMR (CDCl$_3$) δ 1.15 (t,3H), 4.07 (m,1H), 4.33 (m,1H), 4.93 (m,1H), 6.98 (s,1H), 7.21 (d,1H), 7.62 (m,1H), 7.65 (s,1H), 7.77 (m,1H), 7.86 (d,1H), 8.22 (d,1H), 8.28 (d,1H), 9.35 (d,1H). Mass spectrum: (M+H)+ =563.

Anal. Calcd. for C$_{30}$H$_{38}$N$_6$O$_5$.1.35 H$_2$O: C, 61.39; H, 6.99; N, 14.32. Found: C, 60.99; H, 6.58; N, 14.15.

EXAMPLE 110

N-(Quinolinyl-2-carbonyl)-His Amide of 2(S)-Amino-1-cyclohexyl-3(R),4(S)-dihydroxy-6-methylheptane Using the procedure of Example 35 but replacing indole-2-carboxylic acid with quinoline-2-carboxylic acid gave the desired compound (mp 178°–181° C.). $^1$H NMR (CD$_3$OD) δ 0.87 (d,3H), 0.93 (d,3H), 6.98 (s,1H), 7.60 (s,1H), 7.68 (m,1H), 7.83 (m,1H), 7.99 (d,1H), 8.16 (d,1H), 8.18 (d,1H), 8.47 (d,1H). Mass spectrum: (M+H)$^+$ =536.

Anal. Calcd. for C$_{30}$H$_{41}$N$_5$O$_4$.H$_2$O: C, 65.08; H, 7.83; N, 12.65. Found: C, 64.79; H, 7.46; N, 12.56.

EXAMPLE 111

(1'S,2"S,3"R,4"S)-7-Chloro-2-[1-[N-(1-cyclohexyl-3,4-dihydroxy-6-methyl-2-heptyl)carbamoyl]-2-(4-imidazolyl)ethyl]-1,2,3,4-tetrahydropyrrolo[3,4-b]indol-3-one Using the procedures of Examples 99, 100, and 101 but replacing the resultant compound of Example 98 with ethyl 5-chloro-3-formylindole-2-carboxylate (Ishii, et. al., Chem. Pharm. Bull. 1973, 21, 1481) gives the desired compound.

EXAMPLE 112

(1'S,2"S,3"R,4"S)-2-1-N-(1-Cyclohexyl-3,4-dihydroxy-6-methyl-2-heptyl)carbamoyl-2-(4-imidazolyl)ethyl-6-ethoxy-1,2,3,4-tetrahydropyrrolo[3,4-b]indol-3-one Using the procedures of Examples 53, 99, 100, and 101 but replacing benzyl indole-2-carboxylate with ethyl 6-ethoxyindole-2-carboxylate (Ishii, et. al., Chem. Pharm. Bull. 1973, 21, 1481) gives the desired compound.

EXAMPLE 113

N-(1,2,3,4-Tetrahydroisoquinolinyl-2-carbonyl)-histidine Benzyl Ester

Toluene (100 ml) was cooled to 0° C. and treated with gaseous phosgene for 20 min. During the second 10 min period, a solution of 5 ml (40 mmol) of 1,2,3,4-tetrahydroisoquinoline in 50 ml of toluene was added dropwise. After addition was complete, the mixture was warmed in a water bath and nitrogen was bubbled through the solution for 30 min to remove excess phosgene. After filtration, removal of the solvent gave a light brown liquid, a portion of which was taken up in 20 ml of dichloromethane and added dropwise to a precooled (0° C.) solution of 2.00 g (3.4 mmol) of histidine benzyl ester di-p-toluenesulfonate salt and 1.9 ml (13.6 mmol) of triethylamine in 50 ml of dichloromethane. After addition was complete, the resulting solution was stirred at ambient temperature overnight, diluted with dichloromethane, washed with aqueous NaHCO$_3$, dried over MgSO$_4$, and concentrated. Purification by flash column chromatography using 3% methanol in chloroform gave 0.44 g (32%) of the desired compound. $^1$H NMR (CDCl$_3$) δ 2.88 (t,J=6 Hz,2H), 3.11 (d,J=6 Hz,2H), 3.67 (t,J=6 Hz,2H), 4.61 (s,2H), 4.76 (dt,J=8,6 Hz,1H), 5.07 (d,J=12 Hz,1H), 5.19 (d,J=12 Hz,1H), 6.47 (br,1H), 6.57 (s,1H), 7.17 (m,4H), 7.32 (m,5H), 7.51 (s,1H). Mass spectrum: (M+H)$^+$ =405.

EXAMPLE 114

N-(1,2,3,4-Tetrahydroisoquinolinyl-2-carbonyl)-His Amide of 2(S)-Amino-1-cyclohexyl-3(R),4(S)-dihydroxy-6-methylheptane Using the procedure of Example 38 but replacing the resultant compound of Example 37 with the resultant compound of Example 113 gave an intermediate acid in 94% yield which was coupled to the resultant compound of Example 25 using the procedure of Example 35 to give after silica gel chromatography using 7% methanol in chloroform, a 28% yield of the desired compound (mp 114°–116° C. (dec)). $^1$H NMR (CDCl$_3$) δ 0.8–2.0 (br envelope), 0.89 (d,J=7 Hz,3H), 0.95 (d,J=7 Hz,3H), 2.90 (t,J=6 Hz,2H), 3.03 (dd,J=15,7 Hz,1H), 3.13 (dd,J=15,5 Hz,1H), 3.19 (d,J=8 Hz,1H), 3.38 (m,1H), 3.69 (m,2H), 4.33 (m,1H), 4.45 (m,1H), 4.61 (AA',2H), 6.59 (br,1H), 6.91 (br s,1H), 7.19 (m,4H), 7.58 (d,J=1 Hz,1H). Mass spectrum (M+H)$^+$ =540.

Anal. Calcd. for C$_{30}$H$_{45}$N$_5$O$_4$.1.25 H$_2$O: C, 64.09; H, 8.52; N, 12.46. Found: C, 63.96; H, 7.98; N, 12.35.

EXAMPLE 115

N-(1,3-Dihydroisoindolyl-2-carbonyl)-histidine Benzyl Ester

Using the procedure of Example 113 but replacing tetrahydroisoquinoline with dihydroisoindole gives the desired compound.

EXAMPLE 116

N-(1,3-Dihydroisoindolyl-2-carbonyl)-His Amide of 2(S)-Amino-1-cyclohexyl-3(R),4(S)-dihydroxy-6-methylheptane Using the procedure of Example 114 but replacing the resultant compound of Example 113 with the resultant compound of Example 115 gives the desired compound.

EXAMPLE 117

(1'RS,2"S,3"R,4"S)-2-[1-[N-(1-Cyclohexyl-3,4-dihydroxy-6-methyl-2-heptyl)carbamoyl]pentyl]-1,3-dihydro-2H-benz[f]isoindol-1-one Using the procedures of Examples 94, 95, and 96 but replacing 1,2,3,4-tetrahydro-9H-pyrido[3,4-b]indol-1-one with 1,3-dihydro-2H-benz[f]isoindol-1-one (U.S. Pat. No. 3,723,436, issued Mar. 27, 1973) gives the desired compound.

EXAMPLE 118

(1'S,2"S,3"R,4"S)-2-[1-[N-(1-Cyclohexyl-3,4-dihydroxy-6-methyl-2-heptyl)carbamoyl]-2-(4-imidazolyl)ethyl]-6-methyl-1,3-dihydro-2H-pyrrolo[3,4-b]quinolin-3-one Using the procedures of Examples 99 and 101 but replacing the resultant compound of Example 98 with 3-formyl-7-methylquinoline-2-carboxylic acid (Meth-Cohn, et. al., J. Chem. Soc. Perkin Trans. I, 1981, 2509) gives the desired compound.

EXAMPLE 119

(1'S,2"S,3"R,4"S)-2-[1-[N-(1-Cyclohexyl-3,4-dihydroxy-6-methyl-2-heptyl)carbamoyl]-2-(4-imidazolyl)ethyl]-1,3-dihydro-2H-pyrrolo[3,4-b]quinolin-1-one Using the procedures of Examples 99, 100, and 101 but replacing the resultant compound of Example 98 with ethyl 2-formylquinoline-3-carboxylate (Godard, et. al., Bull. Soc. Chim. Fr., 1971, 906) gives the desired compound.

EXAMPLE 120

(Cyclohexyl)methyltriphenylphosphonium Bromide

A solution of 5.80 g (21.9 mmol) of triphenylphosphine and 8.00 g (43.8 mmol) of cyclohexylmethyl bromide in 30 ml of toluene was heated at reflux for 4 days. After removal of solvent in vacuo, the residue was taken up in tetrahydrofuran and filtered to give 6.96 g (37%) of the desired compound.

EXAMPLE 121

Ethyl 3-(3-cyclohexylprop-2-enyl)indole-2-carboxylate

A suspension of 2.00 g (4.7 mmol) of the resultant compound of Example 120 in 20 ml of anhydrous tetrahydrofuran was cooled under $N_2$ atmosphere to $-78°$ C. and treated with 1.72 ml (4.3 mmol) of n-butyllithium in hexane. The resulting solution was stirred at 0° C. for 15 min, treated with 0.45 g (1.96 mmol) of the resultant compound of Example 98, and stirred at 55° C. for 1.5 h. After removal of the solvent in vacuo, the residue was taken up in 100 ml of ethyl acetate, washed with two portions of water and one portion of saturated brine, dried over $MgSO_4$, and concentrated. Purification by silica gel chromatography using 12:1 hexane/ethyl acetate gave 0.30 g (49%) of the desired compound. $^1H$ NMR (CDCl$_3$) δ 1.0–1.4 (m,5H), 1.43 (t,J=7 Hz,3H), 1.72 (m,5H), 2.61 (m,1H), 3.92 (dd,J=7,2 Hz,2H), 4.43 (q,J=7 Hz,2H), 5.28 (ddt,J=11,9,2 Hz,1H), 5.50 (m,1H), 7.13 (ddd,J=8,7,1 Hz,1H), 7.31 (td,J=8,1 Hz,1H), 7.38 (br d,J=8 Hz,1H), 7.70 (br d,J=7 Hz,1H), 8.69 (br,1H). Mass spectrum: (M+H)+=312.

EXAMPLE 122

Ethyl 3-(3-Cyclohexylpropyl)indole-2-carboxylic Acid

Using the procedure of Example 55 with the resultant compound of Example 121 gave the desired compound. $^1H$ NMR (CDCl$_3$) δ 0.87 (m,2H), 1.1–1.4 (m,7H), 1.43 (t,J=7 Hz,3H), 1.7 (m,6H), 3.07 (t,J=7 Hz,2H), 4.41 (q,J=7 Hz,2H), 7.13 (ddd,J=8,7,1 Hz,1H), 7.31 (td,J=8,1 Hz,1H), 7.38 (br d,J=8 Hz,1H), 7.69 (dd,J=8,1 Hz,1H), 8.66 (br,1H). Mass spectrum: (M+H)+=314.

EXAMPLE 123

3-(3-Cyclohexylpropyl)indole-2-carboxylic Acid

Using the procedure of Example 100 with the resultant compound of Example 122 gave the intermediate sodium salt which was acidified, extracted into chloroform, dried over $MgSO_4$, and concentrated to give the desired compound. Mass spectrum: (M+H)+=286.

EXAMPLE 124

His Amide of 3-Amino-1,2-propanediol Dihydrochloride

Using the procedures of Examples 26 and 28 but replacing the resultant compound of Example 25 with 3-amino-1,2-propanediol gave the desired compound.

EXAMPLE 125

N-[3-(3-Cyclohexylpropyl)indolyl-2-carbonyl]-His Amide of 3-Amino-1,2-propanediol The resultant compound of Example 123 was coupled to the resultant compound of Example 124 using the procedure of Example 35 to give the desired compound (mp 98°–100° C.) as a 1:1 mixture of diastereomers in 42% yield after silica gel chromatography using 10%–20% methanol in chloroform. 1H NMR (CDCl$_3$/CD$_3$OD) δ 0.83 (m,2), 1.1–1.3 (m,7H), 1.6–1.7 (m,6H), 3.0 (m,2H), 3.1–3.3 (m,3H), 3.3–3.5 (m,3H), 3.7–3.8 (m,2H), 4.87 (m,1H), 6.82 (s,0.5H), 6.84 (s,0.5H), 7.10 (br t,J=8 Hz,1H), 7.25 (br t,J=8 Hz,1H), 7.35 (br d,J=8 Hz,1H), 7.57 (br s,1H), 7.61 (br d,J=8 Hz,1H). Mass spectrum: (M+H)+=496.

Anal. Calcd. for $C_{27}H_{37}N_5O_4·2H_2O$: C, 61.00; H, 7.77; N, 13.17. Found: C, 61.10; H, 7.16; N, 12.74.

EXAMPLE 126

Ethyl 3-(4-Cyclohexylbut-3-enyl)indole-2-carboxylate

Using the procedure of Example 121 but replacing the resultant compound of Example 98 with the resultant compound of Example 102 gave the desired compound in 83% yield after silica gel chromatography using 12:1 hexane/ethyl acetate. 1H NMR (CDCl$_3$) δ 0.9–1.05 (m,2H), 1.1–1.25 (m,3H), 1.4–1.5 (m,2H). 1.44 (t,J=7 Hz,3H), 1.6–1.7 (m,3H), 2.1–2.2 (m,1H), 2.44 (br q,J=7 Hz,2H), 3.16 (t,J=7 Hz,2H), 4.43 (q,J=7 Hz,1H), 5.19 (ddt,J=11,9,2 Hz,1H), 5.37 (m,1H), 7.15 (ddd,J=8,7,1 Hz,1H), 7.32 (ddd,J=8,7,1 Hz,1H), 7.38 (br d,J=8 Hz,1H), 7.70 (dd,J=8,1 Hz,1H), 8.69 (br,1H). Mass spectrum (M+H)+=326.

EXAMPLE 127

N-[3-(4-Cyclohexylbut-3-enyl)indolyl-2-carbonyl]-His Amide of 3-Amino-1,2-propanediol The resultant compound of Example 126 was hydrolyzed according to the procedure of Example 123 and coupled to the resultant compound of Example 124 using the procedure of Example 35 to give the desired compound (mp 98°–100° C.) as a 1:1 mixture of diastereomers in 36% yield after silica gel chromatography using 10%–20% methanol in chloroform. 1H NMR (CDCl$_3$/CD$_3$OD) δ 0.85–1.0 (m,2H), 1.05–1.4 (m,5H), 1.6–1.7 (m,3H), 2.0–2.1 (m,1H), 2.45 (br q,J=7 Hz,2H), 3.1–3.5 (m,6H), 3.6–3.8 (m,2H), 4.82 (br q,J=6 Hz,1H), 5.18 (br t,J=10 Hz,1H), 5.36 (m,1H), 6.35 (s,0.5H), 6.38 (s,0.5H), 7.13 (br t,J=8 Hz,1H), 7.30 (br t,J=8 Hz,1H), 7.40 (br d,J=8 Hz,1H), 7.66 (br d,J=8 Hz,1H). Mass spectrum (M+H)+=508.

Anal Calcd. for $C_{28}H_{37}N_5O_4·1.5 H_2O$: C, 62.90; H, 7.54; N, 13.10. Found: C, 62.54; H, 7.13; N, 12.52.

EXAMPLE 128

Ethyl 3-(2-Phenylethenyl)indole-2-carboxylate

Using the procedure of Example 121 but replacing the resultant compound of Example 98 with the resultant compound of Example 97 and replacing the resultant compound of Example 120 with benzyltriphenylphosphonium bromide gave the desired compound in 73% yield after silica gel chromatography using 4:1 hexane/ethyl acetate. 1H NMR (CDCl$_3$) δ 1.49 (t,J=7 Hz,3H), 4.48 (q,J=7 Hz,2H), 7.2–7.3 (m,2H), 7.35–7.45 (m,5H), 7.60 (br d,J=8 Hz,1H), 8.07 (d,J=16 Hz,1H), 8.16 (d,J=8 Hz,1H), 8.88 (br,1H). Mass spectrum: (M+H)+=292.

EXAMPLE 129

Ethyl 3-(2-Phenylethyl)indole-2-carboxylate

Using the procedure of Example 38 with the resultant compound of Example 128 gave the desired compound in 83% yield after silica gel chromatography using 4:1 hexane/ethyl acetate. $^1$H NMR (CDCl$_3$) δ 1.44 (t,J=7 Hz,3H), 2.95 (m,2H), 3.40 (m,2H), 4.41 (q,J=7 Hz,1H), 7.1–7.4 (m,8H), 7.65 (br d,J=8 Hz,1H), 8.72 (br,1H). Mass spectrum: (M+H)$^+$ =293.

EXAMPLE 130

[3-(2-Phenylethyl)indolyl-2-carbonyl]-His Amide of 3-Amino-1,2-propanediol

The resultant compound of Example 129 was hydrolyzed according to the procedure of Example 123 and coupled to the resultant compound of Example 124 using the procedure of Example 35 to give the desired compound as a 1:1 mixture of diastereomers (mp 161°–169° C. (dec)) in 29% yield after silica gel chromatography using 20% methanol in chloroform. $^1$H NMR (CDCl$_3$/CD$_3$OD) δ 2.95 (m,2H), 3.1–3.5 (m,6H), 3.18 (m,1H), 3.25 (m,1H), 4.29 (br q,J=6 Hz,1H), 6.82 (s,0.5H), 6.84 (s,0.5H), 7.11 (br t,J=8 Hz,1H), 7.15–7.3 (m,6H), 7.41 (br d,J=8 Hz,1H), 7.51 (br s,1H), 7.61 (br d,J=8 Hz,1H). Mass spectrum: (M+H)$^+$ =476.

EXAMPLE 131

Ethyl 3-(3-Butylaminopropyl)indole-2-carboxylate

Using the procedure of Example 103 but replacing the resultant compound of Example 28 with n-butylamine gives the desired compound.

EXAMPLE 132

N-[3-(3-Butylaminopropyl)indolyl-2-carbonyl]-His Amide of 2(S)-Amino-1-cyclohexyl-3(R),4(S)-dihydroxy-6-methylheptane The resultant compound of Example 131 is hydrolyzed according to the procedure of Example 57 and coupled to the resultant compound of Example 28 using the procedure of Example 35 to give the desired compound.

EXAMPLE 133

5-t-Butyloxycarbonylamino-6-cyclohexyl-2-N-(3-methylbutyl)carboxamido-1-hexen-4-ol-1,2-oxide A solution of the resultant (4S,5S) diastereomer of Example 18 (206 mg, 0.50 mmol) in 8 ml of dichloromethane was treated with 217 mg (1.0 mmol) of 3-chloroperoxybenzoic acid and allowed to stand at rt. After 18 hours, the solution was diluted with 5 ml of ether, treated with 10% aqueous Na$_2$S$_2$O$_3$, stirred vigorously for 1.5 hours, extracted with 25 ml of ether, washed sequentially with 3N NaOH and saturated brine, dried over MgSO$_4$ and concentrated in vacuo to give a 1.1:1 mixture of (2R (R$_f$ 0.49) and (2S) (R$_f$ 0.40, 3:2 chloroform/ethyl acetate) diastereomers, respectively, in 100% yield. The diastereomeric products were separated by flash column chromatography using 5.5:1 chloroform/ethyl acetate. For each isomer, mass spectrum: M$^+$ =426.

EXAMPLE 134

(2S,4S,5S)-N-(3-Methylbutyl)-5-t-butyloxycarbonylamino-6-cyclohexylhexan-2,4-diol-2-carboxamide A suspension of 145 mg (0.34 mmol) of the resultant (2R) diastereomer of Example 135 and 145 mg of 20% palladium on charcoal in 20 ml of methanol was shaken under four atmospheres of H$_2$ for 12 hours. After filtration and concentration in vacuo, purification by silica gel chromatography using 3:1 chloroform/ethyl acetate gave 99 mg (68%) of the desired compound. Mass spectrum: (M+1)$^+$ =429.

EXAMPLE 135

(4S,5S)-N-(3-Methylbuty)-5-t-butyloxycarbonylamino-6-cyclohexylhexan-1,4-diol-2-carboxamide Ammonia (ca. 10 ml) was condensed into a flask containing 10 ml of dry tetrahydrofuran precooled to −78° C. The resulting mixture was treated with ca. 30 mg of lithium metal, stirred at −78° C. for 10 minutes, treated with a solution of the mixture of epoxides produced in Example 133 in 1 ml of tetrahydrofuran, stirred at −78° C. for 6 minutes and cautiously poured into a rapidly stirred mixture of ether and saturated aqueous NH$_4$Cl. The organic layer was separated, dried over MgSO$_4$ and reduced in vacuo. Separation by silica gel chromatography using 1.8:1 chloroform/ethyl acetate followed by 13:1 chloroform/methanol gave a 66% yield (78% based on recovered starting material) of the desired compound as an inseparable 1.5:1 mixture of diastereomers (R$_f$ 0.04, 3:2 chloroform/ethyl acetate). Mass spectrum: (M+1)$^+$ =429.

EXAMPLE 136

5-t-Butyloxycarbonylamino-6-cyclohexyl-2-N-isobutylcarboxamido-1-hexen-4-ol-1,2-oxide Using the procedures of Examples 18 and 133 but replacing N-(3-methylbutyl)-2-methylpropenamide with N-isobutyl-2-methylpropenamide gave, after silica gel chromatography using 5:1 chloroform/ethyl acetate, the desired (2R) (R$_f$ 0.44) and (2S) (R$_f$ 0.37, 3:2 chloroform/ethyl acetate) diastereomeric products in 53% and 47% yields, respectively. For each isomer, mass spectrum: M$^+$ =412.

EXAMPLE 137

(2R,4S,5S)-N-Isobutyl-1-azido-5-t-butyloxycarbonylamino-6-cyclohexylhexan-2,4-diol-2-carboxamide A solution of 51.0 mg (0.124 mmol) of the resultant (2R) diastereomer from Example 136, 24 mg (0.37 mmol) of sodium azide and 15 mg (0.28 mmol) of ammonium chloride in 7 ml of methanol was heated at reflux for 18 hours. The resulting mixture was partitioned between chloroform and water, dried over Na$_2$SO$_4$ and reduced to give a 98% yield of the desired compound which was homogeneous by tlc (R$_f$ 0.54, 3:2 chloroform/ethyl acetate). Mass spectrum: (M+1)$^+$ =456.

EXAMPLE 138

(1'S,2"S,4"S,5"S)-2-[1-[N-[6-Cyclohexyl-2,4-dihydroxy-2-[N-(3-methylbutyl)carbamoyl]hex-5-yl]carbamoyl]-2-(4-imidazolyl)ethyl]-1,2,3,4-tetrahydropyrrolo[3-4-b]indol-3-one Using the procedures of Examples 25 and 35 but replacing indole-2-carboxylic acid with the resultant compound of Example 57 and replacing the resultant compound of Example 20 with the resultant compound of Example 134 gives the desired compound.

EXAMPLE 139

(1'S,4"S,5"S)-2-[1-[N-[6-Cyclohexyl-1,4-dihydroxy-2-[N-(3-methylbutyl)carbamoyl]hex-5-yl]carbamoyl]-2-(4-imidazolyl)ethyl]-1,2,3,4-tetrahydropyrrolo[3,4-b]indol-3-one Using the procedures of Examples 25 and 35 but replacing indole-2-carboxylic acid with the resultant compound of Example 57 and replacing the resultant compound of Example 20 with the resultant compound of Example 135 gives the desired compound.

EXAMPLE 140

(1'S,2"S,4"S,5"S)-2-[1-[N-[1-Chloro-6-cyclohexyl-2,4-dihydroxy-2-(N-isobutylcarbamoyl)hex-5-yl]carbamoyl]-2-(4-imidazolyl)ethyl]-1,2,3,4-tetrahydropyrrolo[3,4-b]indol-3-one Using the procedures of Examples 25 and 35 but replacing indole-2-carboxylic acid with the resultant compound of Example 57 and replacing the resultant compound of Example 20 with the resultant (4R)-diastereomer of Example 136 gives the desired compound.

EXAMPLE 141

(1'S,2"R,4"S,5"S)-2[-1-[N-[1-Azido-6-cyclohexyl-2,4-dihydroxy-2-(N-isobutylcarbamoyl)hex-5-yl]carbamoyl]-2-(4-imidazolyl)ethyl]-1,2,3,4-tetrahydropyrrolo[3,4-b]indol-3-one Using the procedures of Examples 25 and 35 but replacing indole-2-carboxylic acid with the resultant compound of Example 57 and replacing the resultant compound of Example 20 with the resultant compound of Example 137 gives the desired compound.

EXAMPLE 142

3-[3(R)-[3-(tert-Butyloxycarbonyl)-2,2-dimethyl-4(S)-cyclohexylmethyl-5(R)-oxazolidinyl]-3-hydroxy-2(R)-isopropyl-1-oxopropyl]-4(R)-methyl-5(S)-phenyl-2-oxazolidinone Prepared from (S)-cyclohexylalaninol in analogy to the procedure of S. Thaisrivongs, D. T. Pals, L. T. Knoll, S. R. Turner, and F. S. Han, *J. Med. Chem.*, 1987, 30, 976-982.

$^1$H NMR (CDCl$_3$) δ 0.91 (d,3H), 1.06(d,3H), 1.1 (d,3H), 0.9-1.4 (several bm), 1.48 (2S,9H), 1.5-1.9 (several bm), 2.12 (bd,1H), 2.3 (m,1H), 3.81 (dd,1H), 3.94 (td,1H), 4.04 (bm,1H), 4.22 (dd,1H), 4.84 (dq,1H), 5.61 (d,1H), 7.31-7.45 (m,5H); $^{13}$C NMR (CDCl$_3$) δ 14.72, 19.43, 20.09, 26.02, 26.30, 26.43, 26.49, 26.88, 27.51, 28.48 (3C), 29.00, 32.51, 34.37, 34.76, 50.78, 54.89, 56.15, 70.63, 78.47, 79.81, 81.64, 94.24, 125.61 (2C), 128.70 (2C), 128.75, 133.31, 151.64, 152.54, 173.40. Mass spectrum: (M+H)+ =587.

EXAMPLE 143

3-[3(R)-[3-(tert-Butyloxycarbonyl)-2,2-dimethyl-4(S)-cyclohexylmethyl-5-(R)-oxazolidinyl]-3-[(1-imidazolyl)thionyloxy]-2(R)-isopropyl-1-oxopropyl]-4(R)-methyl-5(S)-phenyl-2-oxazolidinone The resultant compound from Example 142 (1.840 g, 3.136 mmol) and 1,1'-thiocarbonyldiimidazolide (1.128 g, 6.330 mmol) were refluxed in 8 ml dry 1,2-dichloroethane under a nitrogen atmosphere for 24 h. The mixture was concentrated and the residue was purified by flash chromatography on silica gel (2.5% methanol in dichloromethane), affording 1.896 g (87%) of the desired compound. $^1$H NMR (CDCl$_3$) δ 0.93 (d,3H), 1.04 (d,3H), 1.08 (d,3H), 0.9-1.1 (bm), 1.1-1.4 (bm), 1.5 (bs,9H), 1.6-1.9 (several bm), 2.05 (m,1H), 4.13 (bm,1H), 4.23 (dd,1H), 4.81 (dd,1H), 4.94 (dq,1H), 5.70 (d,1H), 6.33 (dd,1H), 7.06 (bs,1H), 7.3-7.5 (m,5H), 7.61 (bs,1H), 8.40 (bs,1H). Mass spectrum: (M+H)+ =697.3629. Calcd. for C$_{37}$H$_{53}$N$_4$O$_7$S: 697.3635.

EXAMPLE 144

3-[3-[3-(tert-Butyloxycarbonyl)-2,2-dimethyl-4(S)-cyclohexylmethyl-5(S)-oxazolidinyl]-2(R)-isopropyl-1-oxopropyl]-4(R)-methyl-5(S)-phenyl-2-oxazolidinone The resultant product from Example 143 (129 mg, 0.185 mmol) was dissolved in 10 ml dry toluene and added slowly dropwise over 30 min to a refluxing solution of tri-n-butyltin hydride (93 μl, 100 mg, 0.346 mmol) in 15 ml dry toluene under a nitrogen atmosphere. Reflux was continued for an additional 10 h. The resulting solution was cooled, concentrated in vacuo, and the residue was triturated with four 10 ml portions of acetonitrile, with gentle warming. The combined acetonitrile extracts were washed with three 20 ml portions of hexane, then the combined hexane phases were back-extracted with 20 ml of acetonitrile. All acetonitrile phases were combined and concentrated in vacuo. The crude product was purified by silica gel chromatography (hexane-ethyl acetate 9:1) to give 73 mg (69%) of the desired product. $^1$H NMR (CDCl$_3$) δ 0.90 (d,3H), 0.92 (d,3H), 0.9-1.1 (bm,3H), 1.06 (d,3H), 1.15-1.35 (bm,3H), 1.51 (bs,9H), 1.57-2.14 (several bm), 3.84 (m,1H), 3.97 (m,1H), 4.85 (dq,1H), 5.68 (d,1H), 7.3-7.46 (m,5H). Mass spectrum: (M+H)+ =571.

EXAMPLE 145

2(S)-[3-(tert-Butyloxycarbonyl)-2,2-dimethyl-4(S)-cyclohexylmethyl-5(S)-oxazolidinyl]methyl]-3-methylbutanoic acid The resultant product from Example 144 (842 mg, 1.476 mmol) was dissolved in 15 ml tetrahydrofuran and 5 ml water, and treated with a solution of lithium hydroxide manohydrate (125 mg, 2.98 mmol) in 30% aqueous hydrogen peroxide (1.1 ml, 366 mg hydrogen peroxide, 10.77 mmol). The resulting mixture was stirred 21 h at ambient temperature. The mixture was cooled to 0° and treated with 8.6 ml of 1.5M aqueous sodium sulfite. After 3 h, the mixture was concentrated in vacuo, then the aqueous residue was diluted with 35 ml dichloromethane, cooled to 0°, and acidified to pH 2 with 1M aqueous sodium bisulfate. The crude product was isolated by extraction with four 50 ml portions of dichloromethane, which were combined, washed with 50 ml brine and dried over magnesium sulfate. Concentration and silica gel chromatography of the residue gave 471 mg (77%) of the desired product. $^1$H NMR (CDCl$_3$) δ 0.96 (d,3H), 1.00 (d,3H), 1.1-1.3 (bm,5H), 1.48 (s,9H), 1.5-1.9 (several bm,15H), 2.0 (m,1H), 2.66 (m,1H), 3.7 (bm,1H), 3.90 (m,1H). Mass spectrum (M+H)+ =412.

EXAMPLE 146

Butyl 2(S)-[[3-(tert-butyloxycarbonyl)-2,2-dimethyl-4(S)-cyclohexylmethyl-5(S)-oxazolidinyl]methyl]-3-methylbutanamide The resultant product from Example 145 (446 mg, 1.085 mmol) was treated with 1-hydroxybenztriazole monohydrate (216 mg, 1.41 mmol), 4-methylmorpholine (285 mg, 2.82 mmol) and 1-(dimethylamino propyl)-3-ethylcarbodiimide hydrochloride (301 mg, 1.10 mmol) in 10 ml anhydrous dimethylformamide at −20°, under a nitrogen atmosphere. The reaction solution was stirred at −20° for 10 min, then allowed to react at 0° for 3 days. To this solution was added n-butylamine (163 mg, 2.22 mmol), and the resulting solution was stirred at 0° for 2 h, then at ambient temperature for an additional 22 h. The solution was concentrated, and the residue partitioned between 30 ml sat. aqueous sodium bicarbonate and 50 ml ethyl acetate. The aqueous layer was further extracted with three 30 ml portions of ethyl acetate, and the combined organic phases were washed with 50 ml brine, dried over sodium sulfate and concentrated in vacuo. Purification by silica gel chromatography (ethyl acetate-hexane 1:4) afforded 483 mg (95%) of the desired product. $^1$H NMR (CDCl$_3$) δ 0.91 (t,3H), 0.93 (d,3H), 0.95 (d,3H), 1.1–1.3 (m,4H), 1.3–1.9 (several m, approximately 21H), 1.49 (s,9H), 2.0 (m,1H), 3.28 (qd,2H), 3.63 (bm,1H), 3.75 (ddd,1H), 5.63 (bt,1H); $^{13}$C NMR (CDCl$_3$) δ 13.71, 20.12, 20.30, 21,06, 26.09, 26.28, 26.60, 27.99, 28.62 (3C), 30.68, 31.94, 32.81, 34.54, 35.01, 36.21, 39.12, 51.02, 61.21, 79.05, 79.76, 93.80, 152.02, 174.53.

EXAMPLE 147

(1′S,3″S,5″S,6″S)-2-[N-[3-(N-Butylcarbamoyl)-7-cyclohexyl-5-hydroxy-1-methylhept-6-yl]carbamoyl]-2-(4-imidazolyl)ethyl]-1,2,3,4-tetrahydropyrrolo[3,4-b]indol-3-one Using the procedures of Examples 25 and 35 but replacing indole-2-carboxylic acid with the resultant compound of Example 57 and replacing the resultant compound of Example 20 with the resultant compound of Example 146 gives the desired compound.

EXAMPLE 148

Cbz-(O-methoxymethyl)serine Methyl Ester

A solution of 4.86 g (19 mmol) of Cbz-serine methyl ester in 5 ml of dichloromethane was cooled to 0° C. and treated successively in a dropwise fashion with 3.2 ml (42 mmol) of chloromethyl methyl ether and 7.4 ml (42 mmol) of diisopropylethylamine. After being allowed to stir at ambient temperature for 16 h, the solution was diluted with dichloromethane, washed successively with 5% HCl, 5% NaHCO$_3$, and saturated brine; dried, and concentrated to a yellow liquid. Silica gel chromatography using ethyl acetate/chloroform gave 3.9 g (69%) of the desired compound.

EXAMPLE 149

Cbz-(O-methoxymethyl)Ser Amide of 2(S)-Amino-1-cyclohexyl-3(R),4(S)-dihydroxy-6-methylheptane The resultant compound of Example 148 was hydrolyzed according to the procedure of Example 57 and coupled to the resultant compound of Example 25 using the procedure of Example 35 to give the desired compound in 77% yield.

EXAMPLE 150

N-(Indolyl-2-carbonyl)-(O-methoxymethyl)Ser Amide of 2(S)-Amino-1-cyclohexyl-3(R),4(S)-dihydroxy-6-methylheptane The resultant compound of Example 149 was hydrogenolyzed according to the V procedure of Example 55 and coupled to indole-2-carboxylic acid using the procedure of Example 35 to give the desired compound in 72% after silica gel chromatography using 2% methanol in chloroform. $^1$H NMR (CDCl$_3$) δ 0.8–2.0 (br envelope), 0.91 (d,J=7 Hz,3H), 0.98 (d,J=7 Hz,3H), 3.26 (m,1H), 3.35 (m,1H), 3.42 (s,3H), 3.77 (dd,J=10,7 Hz,1H), 4.02 (br,1H), 4.17 (dd,J=10,4 Hz,1H), 4.41 (m,1H), 4.71 (AA′,2H), 4.81 (m,1H), 6.52 (br d,J=10 Hz,1H), 7.01 (d,J=2 Hz,1H), 7.18 (br t,J=8 Hz,1H), 7.32 (m,2H), 7.45 (br d,J=8 Hz,1H), 7.69 (br d,J=8 Hz,1H), 9.29 (br s,1H). Mass spectrum: (M+H)$^+$ =518.

Anal. Calcd. for C$_{28}$H$_{43}$N$_3$O$_6$.0.5 H$_2$O: C, 63.86; H, 8.42; N, 7.98. Found: C, 63.66; H, 8.27; N, 8.00.

EXAMPLE 151

N-(2-Napthoyl)-His Amide of 2(S)-Amino-1-cyclohexyl-3(R),4(S)-dihydroxy-6-methylheptane Using the procedure of Example 35 but replacing indole-2-carboxylic acid with 2-napthoic acid gave the desired compound. Rf (5:1 CH$_2$Cl$_2$-MeOH) 0.34; $^1$H NMR (d$_6$-DMSO) δ 0.78 (d,J=7 Hz,3H), 0.88 (d,J=7 Hz,3H), 1.0–1.9 (br envelope), 2.9–3.2 (m,4H), 4.1–4.2 (m,1H), 4.7–4.82 (m,2H), 7.54–7.65 (m,3H), 7.91 (dd,J=9,1 Hz,1H), 7.95–8.05 (m,3H), 8.43 (br s,1H), 8.84 (br d,J=8 Hz,1H). Mass spectrum: (M+H)$^+$ =535.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptonate, glycerophosphate, hemisulfate, heptonate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

The compounds of the present invention can also be used in the form of esters. Examples of such esters include a hydroxyl-substituted compound of formula I which has been acylated with a blocked or unblocked amino acid residue, a phosphate function, or a hemisuccinate residue. The amino acid esters of particular interest are glycine and lysine; however, other amino acid residues can also be used. These esters serve as pro-drugs of the compounds of the present invention and serve to increase the solubility of these substances in the gastrointestinal tract. The preparation of the pro-drug esters is carried out by reacting a hydroxyl-substituted compound of formula I with an activated amino acyl, phosphoryl or hemisuccinyl derivative. The resulting product is then deprotected to provide the desired pro-drug ester.

The novel compounds of the present invention possess an excellent degree of activity and specificity in treating renin-associated hypertension in a host. The ability of the compounds of the invention to inhibit human renal renin can be demonstrated in vitro by reacting a selected compound at varied concentrations with human renal renin, free from acid proteolytic activity, and with renin substrate (human angiotensinogen) at 37 degrees C and pH of 6.0. At the end of the incubation, the amount of angiotensin I formed is measured by radioimmunoassay and the molar concentration required to cause 50% inhibition, expressed as the $IC_{50}$, is calculated. When tested in accordance with the foregoing procedure, the compounds of the invention demonstrated $IC_{50}$'s in the range of $10^{-6}$ to $10^{-10}$ M as seen in Table I.

TABLE I

| Example | $IC_{50}(nM)$ |
| --- | --- |
| 35 | 3.3 |
| 37 | 130 |
| 38 | 130 |
| 40 | 15 |
| 41 | 160 |
| 42 | 200 |
| 43 | 10 |
| 45 | 31 |
| 48 | 170 |
| 51 | 12 |
| 58 | 8.2 |
| 59 | 19 |
| 70 | 100 |
| 75 | 200 |
| 81 | 5 |
| 87 | 9.5 |
| 88 | 28 |
| 89 | 89 |
| 93 | 44 |
| 96 | 66 |
| 101 | 67 |
| 109 | 36 |
| 110 | 8.7 |
| 114 | 63 |
| 125 | 3800 |
| 127 | 7000 |
| 130 | 10000 |
| 150 | 27 |
| 151 | 32 |

The compounds of the invention may also be used with one or more antihypertensive agents selected from the group of diuretics, and/or β-adrenergic blocking agents, central nervous system-acting agents, adrenergic neuron blocking agents, vasodilators, angiotensin I converting enzyme inhibitors, and other antihypertensive agents.

Total daily dose administered to a host in single or divided doses may be in amounts, for example, from 0.001 to 10 mg/kg body weight daily and more usually 0.01 to 10 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjuvants, and vehicles as desired. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The foregoing is merely illustrative of the invention and is not intended to limit the invention to the disclosed compounds. Variations and changes which are obvious to one skilled in the art are intended to be

What is claimed is:

1. A compound of the formula:

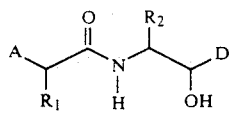

wherein A is

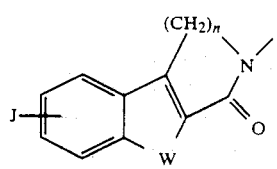

wherein J is absent or represents one or two substituents independently selected from hydroxy, loweralkoxy, amino, loweralkylamino, diloweralkylamin loweralkyl, thioloweralkoxy and halo; W is $NR_4$ wherein $R_4$ is hydrogen, loweralkyl or arylloweralkyl wherein aryl is selected from phenyl, naphthyl, substituted phenyl and substituted naphthyl wherein the phenyl or naphthyl ring is substituted with loweralkyl, amino, (N-protected)amino, loweralkylamino, diloweralkylamino, loweralkoxy, thioloweralkoxy, hydroxy, halo, mercapto, nitro, carboxaldehyde, carboxyl, loweralkoxycarbonyl or carboxamide; n is 1; $R_1$ is heterocyclic substituted methyl wherein the heterocycle is a 5-membered ring containing one oxygen, sulfur or nitrogen atom; or one nitrogen and one oxygen atom; or two or three nitrogen atoms; $R_2$ is hydrogen, loweralkyl, $C_4$ to $C_7$ cycloalkylmethyl or benzyl; and D is

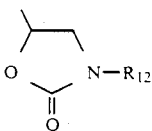

wherein $R_{12}$ is hydrogen, loweralkyl, hydroxyloweralkyl, hydroxy, loweralkoxy, amino or loweralkylamino; or a pharmaceutically acceptable salt or ester thereof.

2. The compound of claim 1 wherein $R_1$ is imidazolylmethyl, pyrazolylmethyl or 2-thienylmethyl, $R_2$ is cyclohexylmethyl and D is

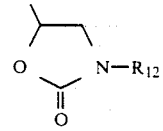

wherein $R_{12}$ is hydrogen, loweralkyl, loweralkoxy or loweralkylamino.

3. The compound (1'S,2"S,3"R,5"'S)-2-(1-(N-(1-cyclohexyl-3-hydroxy-3-(3-ethyloxazolidin-2-on-5-yl)-2-propyl)carbamoyl-2-(4-imidazolyl)methyl)-1,2,3,4-tetrahydropyrrolo(3,4-b)-indole-3-one.

4. A pharmaceutical composition for treating hypertension, comprising a pharmaceutical carrier and a therapeutically effective amount of a compound of claim 1.

5. A method for treating hypertension comprising administering to a host in need of such treatment a therapeutically effective amount of a compound of claim 1.

6. A pharmaceutical composition for inhibiting renin comprising a pharmaceutical carrier and a therapeutically effective amount of a compound of claim 1.

7. A method for inhibiting renin comprising administering to a host in need of such treatment a therapeutically effective amount of a compound of claim 1.

* * * * *

UNITED STATES PATENT AND TRADEMARK OFFICE
CERTIFICATE OF CORRECTION

PATENT NO. : 4,994,477

DATED : February 19, 1991

INVENTOR(S) : DALE J. KEMPF

It is certified that error appears in the above-identified patent and that said Letters Patent is hereby corrected as shown below:

On title page, column 1, line 2, delete "Saul H. Rosenberg;

Jacob J. Plattner, both of Libertyville; Hing L. Shan, Gurnee;

Biswanath De, Vernon Hills,"

Column 1, line 25, Replace "diloweralkylamin" with

--diloweralkylamino--.

Signed and Sealed this

Eleventh Day of August, 1992

Attest:

DOUGLAS B. COMER

*Attesting Officer*  *Acting Commissioner of Patents and Trademarks*